United States Patent
McKinney et al.

(10) Patent No.: US 9,402,910 B2
(45) Date of Patent: Aug. 2, 2016

(54) INTERNALLY FUNCTIONALIZED GRAPHENE SUBSTRATES

(71) Applicant: NANOTECH BIOMACHINES, INC., Berkeley, CA (US)

(72) Inventors: Jeffrey Alan McKinney, Lafayette, CA (US); William Emerson Martinez, Berkeley, CA (US)

(73) Assignee: Nanotech Biomachines, Inc., Berkeley, CA (US)

( * ) Notice: Subject to any disclaimer, the term of this patent is extended or adjusted under 35 U.S.C. 154(b) by 0 days.

(21) Appl. No.: 14/120,928

(22) Filed: Jul. 9, 2014

(65) Prior Publication Data

US 2015/0017699 A1    Jan. 15, 2015

Related U.S. Application Data

(60) Provisional application No. 61/957,816, filed on Jul. 12, 2013.

(51) Int. Cl.
| | | |
|---|---|---|
| *A61K 47/48* | (2006.01) | |
| *A61K 31/7088* | (2006.01) | |
| *A61K 31/7016* | (2006.01) | |
| *A61K 31/702* | (2006.01) | |
| *C12N 11/02* | (2006.01) | |
| *C01B 31/04* | (2006.01) | |
| *A61K 38/00* | (2006.01) | |

(52) U.S. Cl.
CPC ......... *A61K 47/48015* (2013.01); *A61K 31/702* (2013.01); *A61K 31/7016* (2013.01); *A61K 31/7088* (2013.01); *C01B 31/0484* (2013.01); *C12N 11/02* (2013.01); *A61K 38/00* (2013.01)

(58) Field of Classification Search
CPC .............................................. A61K 47/48015
See application file for complete search history.

(56) References Cited

FOREIGN PATENT DOCUMENTS

WO    WO 2008/104078 A1    9/2008

OTHER PUBLICATIONS

Pumera, 2011, Graphene in biosensing, Materials Today, 14(7-8): 308-315.*
Kodali et al., 2011, Nonperturbative Chemical Modification of Graphene for Protein Micropatterning, Langmuir, 27(3): 863-865.*
Sardesai et al., 2011, Carbon Nanotube Microwell Array for Sensitive Electrochemiluminescent Detection of Cancer Biomarker Proteins, Anal. Chem., 83: 6698-6703.*

* cited by examiner

*Primary Examiner* — Amber D Steele
(74) *Attorney, Agent, or Firm* — Fenwick & West LLP

(57) ABSTRACT

The present invention is generally directed to internally functionalized graphene substrates, methods of making such substrates and methods of using such substrates. In one aspect, the present invention is a graphene substrate. The substrate comprises edge and non-edge regions. Organic or inorganic molecules are bound to the non-edge regions of the substrate, and the organic or inorganic molecules are present on the substrate edges at a population greater than about one molecule per 10,000 $nm^2$.

25 Claims, 22 Drawing Sheets

INTERNALLY FUNCTIONALIZED GRAPHENE SUBSTRATES

This application claims priority from U.S. Provisional Patent Appl. No. 61/957,816, filed Jul. 12, 2013, entitled, "Internally Functionalized Graphene Substrates", which is hereby incorporated by reference into this application in its entirety.

FIELD OF THE INVENTION

The present invention is generally directed to internally functionalized graphene substrates, methods of making such substrates and methods of using such substrates.

BACKGROUND OF THE INVENTION

Discussions regarding specific properties of graphene have been reported. For instance, U.S. Pat. No. 8,461,028, issued Jun. 11, 2013 and entitled "Synthesizing Graphene from Metal-Carbon Solutions Using Ion Implantation", discusses the following: "A method and semiconductor device for synthesizing graphene using ion implantation of carbon. Carbon is implanted in a metal using ion implantation. After the carbon is distributed in the metal, the metal is annealed and cooled in order to precipitate the carbon from the metal to form a layer of graphene on the surface of the metal. The metal/graphene surface is then transferred to a dielectric layer in such a manner that the graphene layer is placed on top of the dielectric layer. The metal layer is then removed. Alternatively, recessed regions are patterned and etched in a dielectric layer located on a substrate. Metal is later formed in these recessed regions. Carbon is then implanted into the metal using ion implantation. The metal may then be annealed and cooled in order to precipitate the carbon from the metal to form a layer of graphene on the metal's surface." Abstract.

U.S. Pat. No. 8,414,799, issued Apr. 9, 2013 and entitled "Method for Manufacturing Graphene", discusses the following: "A method for manufacturing graphene is disclosed, which comprises the following steps: putting graphite material and an organic solvent, a surfactant, or a combination thereof in a reaction tank and introducing a supercritical fluid in the reaction tank to allow the organic solvent, the surfactant, or the combination thereof to dissolve in the supercritical fluid and to permeate into the graphite material; and removing the supercritical fluid by depressurization to form graphene. The method of the present invention has simple steps and reduced consumption of manufacturing time, and also can promote the quality of the resultant graphene in large-scale manufacturing." Abstract.

U.S. Pat. No. 8,361,813, issued Jan. 29, 2013 and entitled "Method for Generating Graphene Structures", discusses the following: "A method for depositing graphene is provided. The method includes depositing a layer of non-conducting amorphous carbon over a surface of a substrate and depositing a transition metal in a pattern over the amorphous carbon. The substrate is annealed at a temperature below 500° C., where the annealing converts the non-conducting amorphous carbon disposed under the transition metal to conducting amorphous carbon. A portion of the pattern of the transition metal is removed from the surface of the substrate to expose the conducting amorphous carbon." Abstract.

Despite the reported discussions, there is still a need in the art for new internally functionalized graphene substrates, methods of making such substrates and methods of using such substrates.

SUMMARY OF THE INVENTION

In one aspect, the present invention is a graphene substrate. The substrate comprises edge and non-edge regions. Organic or inorganic molecules are bound to the non-edge regions of the substrate, and the organic or inorganic molecules are present on the substrate edges at a population greater than about one molecule per 10,000 $nm^2$.

In another aspect, the present invention is a method of functionalizing a graphene substrate. The method comprises the steps of: obtaining a graphene substrate that has edge regions and non-edge regions, where the non-edge regions comprise epoxy moieties; reacting the epoxy moieties with a Nu-M, wherein Nu is a nucleophilic moiety and M is an attached organic or inorganic moiety, thereby functionalizing the graphene substrate.

In another aspect, the present invention is a method of functionalizing a graphene substrate. The method comprises the steps of: obtaining a graphene substrate that has edge regions and non-edge regions, where the non-edge regions comprise hydroxy moieties; reacting the hydroxyl moieties with a E-M, wherein E is an electrophilic moiety and M is an attached organic or inorganic moiety, thereby functionalizing the graphene substrate.

In another aspect, the present invention is a method of functionalizing a graphene substrate. The method comprises the steps of: obtaining a graphene substrate that has edge regions and non-edge regions; reacting the substrate with a molecule that comprises a histidine, arginine, lysine or cationic tag covalently attached to it, thereby providing a functionalized graphene substrate, where molecules are non-covalently attached to the non-edge regions of the substrate.

DETAILED DESCRIPTION OF THE INVENTION

Figure 1:
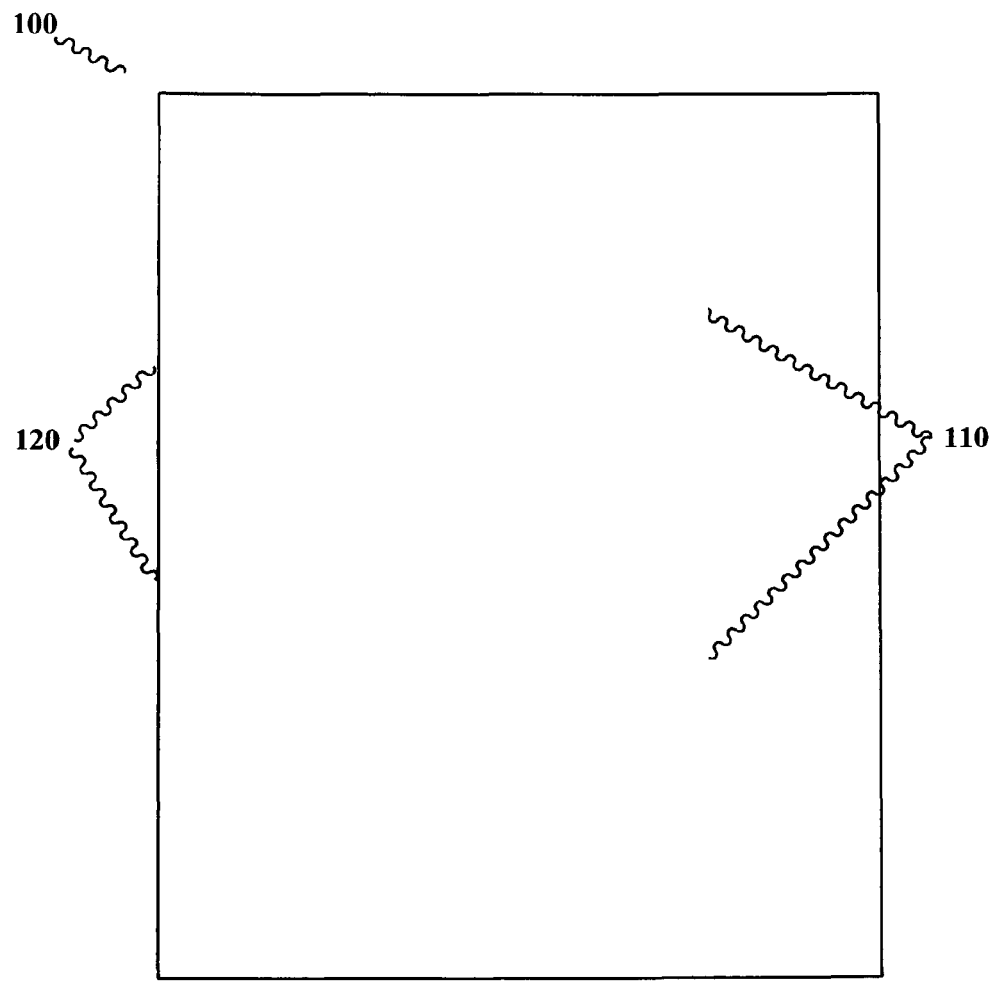
FIG. 1 is an illustration of a graphene substrate (100) having non-edge regions (110) and edge regions (120).

The present invention is generally directed to internally functionalized graphene substrates, methods of making such substrates and methods of using such substrates.

Definitions

"Amino acid letter code" refers to the one letter code typically used for amino acids: arginine (R); histidine (H); lysine (K); aspartic acid (D); glutamic acid (E); serine (S); threonine (T); asparagine (N); glutamine (Q); cysteine (C); glycine (G); proline (P); alanine (A); valine (V); isoleucine (I); leucine (L); methionine (M); phenylalanine (F); tyrosine (Y); tryptophan (W).

"Antibody" refers to a Y-shaped protein on the surface of B cells that is secreted into the blood or lymph in response to an antigenic stimulus.

"Antibody fragment" refers to part of an antibody comprising an antigen binding domain.

"Aptamer" refers to small, single-stranded nucleic acids that fold into a well-defined three-dimensional structure. They show a high affinity and specificity for their target molecules and inhibit their biological functions. Aptamers are usually discovered/created by selecting them from a large random sequence pool.

"Arginine tagged" refers to at least one arginine residue that is attached to a molecule to facilitate interaction with a graphene substrate. Arginine tags may be of any appropriate length (e.g., two, three, four, five, six, seven, eight, nine or ten arginine residues).

"Binding site" refers to a region on a molecule (e.g., protein, DNA, RNA) to which other specific molecules and/or ions form one or more chemical bonds, typically non-covalent bonds.

"Cation tagged" refers to the inclusion of at least one cationic residue (e.g., $-NR_3^+$ where R is H or alkyl) to a molecule to facilitate interaction with a graphene substrate. Nonlimiting examples of such tags include $-NH_3^+$, $-N(CH_3)_3^+$, and $-N(CH_2CH_3)_3^+$.

"Covalently" bound refers to formation of a covalent bond, which involves the sharing of electrons between at least two atoms. The strength of a covalent bond typically ranges from approximately 50 kcal/mol to approximately 100 kcal/mol.

"Edge region" of a graphene substrate refers to a line or border where the graphene substrate ends and either another material or an open space begins. Graphene edge regions typically include oxidized carbon moieties such as carboxylic acids, epoxides and hydroxyl groups.

"Graphene nanomesh" refers to a one atom thick layer of carbon atoms including holes in a repeating structural fashion (e.g., honeycomb structure).

"Graphene nanoribbon" refers to strips of graphene having ultra-thin widths (e.g., <50 nm).

"Graphene substrate" refers to a layer of carbon atoms, typically one, two, three or four atoms thick. There are at least 100 carbon atoms in the substrate. Monolayer graphene refers to a substrate that is one carbon atom thick.

"Histidine tagged" refers to at least one histidine residue that is attached to a molecule to facilitate interaction with a graphene substrate. Histidine tags may be of any appropriate length (e.g., two, three, four, five, six, seven, eight, nine or ten histidine residues).

"Hydrogen bond" refers to a noncovalent bond formed by the interaction of a proton on one molecule and an electronegative atom on another. The strength of a hydrogen bond typically ranges from approximately 3 kcal/mol to approximately 10 kcal/mol.

"Inorganic molecule" refers to molecules that do not include carbon atoms.

"Ionically" bound refers to the formation of an ionic bond. The strength of an ionic bond typically ranges from approximately 5 kcal/mol to approximately 10 kcal/mol.

"$K_D$" refers to "dissociation constant", which is a specific type of equilibrium constant that measures the propensity of a larger object to separate (dissociate) reversibly into smaller components, as when a complex falls apart into its component molecules. The dissociation constant is the inverse of the association constant. For a general reaction

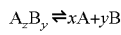

in which a complex $A_xB_y$ breaks down into x A subunits and y B subunits, the dissociation constant is defined $$K_d = \frac{[A]^x \times [B]^y}{[A_xB_y]}$$

where [A], [B], and [$A_xB_y$] are the concentrations of A, B, and the complex $A_xB_y$, respectively.

"Large molecule therapeutic" refers to an organic molecule of molecular weight greater than 1000 g/mol, where the molecule has been, or is currently, used for a clinical application. Nonlimiting examples of large molecule therapeutic classes include: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-glucosidase inhibitors; amebicides; aminoglycosides; aminopenicillins; aminosalicylates; AMPA receptor antagonists; amylin analogs; analgesics; androgens and anabolic steroids; angiotensin converting enzyme inhibitors; angiotensin II inhibitors; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiarrheals; antidiuretic hormones; antiemetic/antivertigo agents; antifungals; antigonadotropic agents; antigout agents; antihistamines; antihyperlipidemic agents; antihyperuricemic agents; antimalarial agents; antimalarial combinations; antimalarial quinolines; antimetabolites; antimigraine agents; antineoplastic detoxifying agents; antineoplastic interferons; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; bisphosphonates; bone resorption inhibitors; bronchodilators; calcineurin inhibitors; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD30 monoclonal antibodies; CD33 monoclonal antibodies; CD52 monoclonal antibodies; central nervous system agents; cephalosporins; cerumenolytics; CFTR potentiators; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; dibenzazepine anticonvulsants; digestive enzymes; dipeptidyl peptidase 4 inhibitors; diuretics; dopaminergic antiparkinsonism agents; echinocandins; EGFR inhibitors; estrogen receptor antagonists; estrogens; factor Xa inhibitors; fatty acid derivative anticonvulsants; fibric acid derivatives; first generation cephalosporins; fourth generation cephalosporins; gamma-aminobutyric acid analogs; gamma-aminobutyric acid reuptake inhibitors; gastrointestinal agents; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; guanylate cyclase-C agonists; *H. pylori* eradication agents; H2 antagonists; hedgehog pathway inhibitorshematopoietic stem cell mobilizer; heparin antagonists; heparins; HER2 inhibitors; histone deacetylase inhibitors; hormones; hormones/antineoplastics; hydantoin anticonvulsants; hydrazide derivatives; immune globulins; immunologic agents; immunostimulants; immunosuppressive agents; incretin mimetics; inotropic agents; insulin; insulin-like growth factor; integrase strand transfer inhibitor; interferons; interleukin inhibitors; interleukins; ketolides; leprostatics; leukotriene modifiers; lincomycin derivatives; loop diuretics; lymphatic staining agents; lysosomal enzymes; macrolide derivatives; macrolides; mast cell stabilizers; meglitinides; metabolic agents; methylxanthines; mineralocorticoids; mitotic inhibitors; monoamine oxidase inhibitors; mTOR inhibitors; mucolytics; multikinase inhibitors; muscle relaxants; mydriatics; narcotic analgesics; natural penicillins; neuraminidase inhibitors; neuromuscular blocking agents; neuronal potassium channel openers; next generation cephalosporins; nicotinic acid derivatives; NNRTIs; non-cardioselective beta blockers; non-sulfonylureas; nonsteroidal anti-inflammatory agents; nucleoside reverse transcriptase inhibitors (NRTIs); oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proteasome inhibitors; proton pump inhibitors; psoralens; psychotherapeutic agents; purine nucleosides; pyrrolidine anticonvulsants; quinolones; recombinant human erythropoietins; renin inhibitors; respiratory agents; rifamycin derivatives; salicylates; sclerosing agents; second generation cephalosporins; selective estrogen receptor modulators; selective immunosuppressants; selective phosphodiesterase-4 inhibitors; selective serotonin reuptake inhibitors; serotonin-norepinephrine reuptake inhibitors; serotoninergic neuroenteric modulators; sex hormone combinations; sex hormones; SGLT-2 inhibitors; skeletal muscle relaxants; smoking cessation agents; somatostatin and somatostatin analogs; statins; *streptomyces* derivatives; succinimide anticonvulsants; sulfonamides; sulfonylureas; synthetic ovulation stimulants; tetracyclic antidepressants; tetracyclines; therapeutic radiopharmaceuticals; therapeutic vaccines; thiazide diuretics; thiazolidinediones; thioxanthenes; third generation cephalosporins; thrombin inhibitors; thrombolytics; thyroid drugs; TNF alfa inhibitors; tocolytic agents; triazine anticonvulsants; tricyclic antidepressants; trifunctional monoclonal antibodies; urea anticonvulsants; urea cycle disorder agents; urinary anti-infectives; urinary antispasmodics; vasodilators; vasopressin antagonists; vasopressors; VEGF/VEGFR inhibitors; viral vaccines.

"Large organic molecule" refers to an organic molecule of molecular weight greater than 1000 g/mol.

"Linking group" refers to an organic moiety that is used as an intermediate molecular section to attach an organic or inorganic compound to an edge region of a graphene substrate. Nonlimiting examples of linking groups include: —NH(CH$_2$)$_2$NH—; —NH(CH$_2$)$_3$NH—; —NH(CH$_2$)$_4$NH—; —NH(CH$_2$)$_5$NH—; —NH(CH$_2$)$_6$NH—; —NH(CH$_2$)$_2$O—; —NH(CH$_2$)$_3$O—; —NH(CH$_2$)$_4$O—; —NH(CH$_2$)$_5$O—; —NH(CH$_2$)$_6$O—; —NH(CH$_2$)O(CH$_2$)NH—; —NHCH$_2$C(O)—; —NH(CH$_2$)$_2$C(O)—; —NH(CH$_2$)$_3$C(O)—; —NH(CH$_2$)$_4$C(O)—; —NH(CH$_2$)$_5$C(O)—; —NH(CH$_2$)$_6$C(O)—; —NH(CH$_2$)$_2$O(CH$_2$)$_2$OC(O)—; —O(CH$_2$)$_2$NH—; —O(CH$_2$)$_3$NH—; —O(CH$_2$)$_4$NH—; —O(CH$_2$)$_5$NH—; —O(CH$_2$)$_6$NH—; —O(CH$_2$)$_2$O—; —O(CH$_2$)$_3$O—; —O(CH$_2$)$_4$O—; —O(CH$_2$)$_5$O—; —O(CH$_2$)$_6$O—; —O(CH$_2$)O(CH$_2$)NH—; —OCH$_2$C(O)—; —O(CH$_2$)$_2$C(O)—; —O(CH$_2$)$_3$C(O)—; —O(CH$_2$)$_4$C(O)—; —O(CH$_2$)$_5$C(O)—; —O(CH$_2$)$_6$C(O)—; —O(CH$_2$)$_2$—O(CH$_2$)$_2$OC(O)—; —NHC$_6$H$_4$NHC(S)NH(CH$_2$)$_6$—OP(O)$_2$—; —S(CH$_2$)$_6$OP(O)$_2$—; —NH(CH$_2$)$_3$NHC(O)(CH$_2$)$_5$NHC(O)(CH$_2$)S—; —NHNHC(O)—(CH$_2$)$_4$C(O)NH—; —NH(CH$_2$)$_3$NH(CH$_2$)$_3$NH—; —NH(CH$_2$)$_3$NH(CH$_2$)$_3$NHCH$_2$—.

"Lysine tagged" refers to at least one lysine residue that is attached to a molecule to facilitate interaction with a graphene substrate. Lysine tags may be of any appropriate length (e.g., two, three, four, five, six, seven, eight, nine or ten lysine residues).

"Natural binding compound" refers to a ligand for a molecular binding site that is produced by the same organism that produces the molecule with the binding site. Typically, the ligand binds to the binding site with a $K_D$<1 µM or even <100 nM.

"Non-covalently" bound refers to formation of a non-covalent bond, which does not involve the sharing of electrons between at least two atoms. The strength of a covalent bond typically ranges from approximately 1 kcal/mol to approximately 10 kcal/mol.

"Non-edge region" of a graphene substrate refers to the area between lines or borders where the graphene substrate ends and either another material or an open space begins.

"Non-natural binding compound" refers to a synthetically produced ligand for a molecular binding site that is not produced by the same organism that produces the molecule with the binding site. Typically, the ligand binds to the binding site with a $K_D$<1 µM or even <100 nM.

"Nucleic acid letter code" refers to the one letter code typically used for nucleic acids: adenine (A); cytosine (C); guanine (G); thymine (T); uracil (U).

"Oligonucleotide" refers to short single-stranded DNA or RNA molecules. Oligonucleotides typically include between about 2 and about 50 nucleotides, often between about 2 and about 35 nucleotides, and in certain cases between about 2 and about 20 nucleotides.

Where the oligonucleotide is a single stranded DNA molecule, a nonlimiting, generalized structure is as shown below:

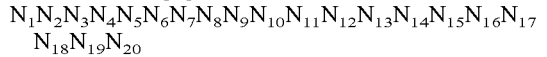

where $N_1$ is A, T, C or G; $N_2$ is A, T, C or G; $N_3$ is A, T, C or G; $N_4$ is A, T, C or G; $N_5$ is A, T, C, G, or no base; $N_6$ is A, T, C, G, or no base; $N_7$ is A, T, C, G, or no base; $N_8$ is A, T, C, G, or no base; $N_9$ is A, T, C, G, or no base; $N_{10}$ is A, T, C, G, or no base; $N_{11}$ is A, T, C, G, or no base; $N_{12}$ is A, T, C, G, or no base; $N_{13}$ is A, T, C, G, or no base; $N_{14}$ is A, T, C, G, or no base; $N_{15}$ is A, T, C, G, or no base; $N_{16}$ is A, T, C, G, or no base; $N_{17}$ is A, T, C, G, or no base; $N_{18}$ is A, T, C, G, or no base; $N_{19}$ is A, T, C, G, or no base; $N_{20}$ is A, T, C, G, or no base.

Where the oligonucleotide is a single stranded RNA molecule, a nonlimiting, generalized structure is as shown below:

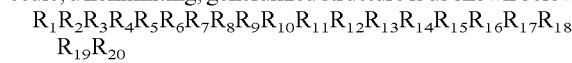

where $R_1$ is A, U, C, or G; $R_2$ is A, U, G, or C; $R_3$ is A, U, G, or C; $R_4$ is A, U, G, or C; $R_5$ is A, U, G, or C; $R_6$ is A, U, G, C or no base; $R_7$ is A, U, G, C or no base; $R_8$ is A, U, G, C or no base; $R_9$ is A, U, G, C or no base; $R_{10}$ is A, U, G, C or no base; $R_{11}$ is A, U, G, C or no base; $R_{12}$ is A, U, G, C or no base; $R_{13}$ is A, U, G, C or no base; $R_{14}$ is A, U, G, C or no base; $R_{15}$ is A, U, G, C or no base; $R_{16}$ is A, U, G, C or no base; $R_{17}$ is A, U, G, C or no base; $R_{18}$ is A, U, G, C or no base; $R_{19}$ is A, U, G, C or no base; $R_{20}$ is A, U, G, C or no base.

"Oligopeptide" refers to a short chain of amino acids. Oligopeptides typically include between about 2 and about 25 amino acids. A nonlimiting, generalized structure for oligopeptides is shown below:

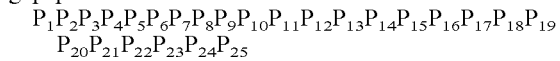

where $P_1$ is G, P, A, V, L, I M, C, R, Y, W, H, K, R, Q, N, E, D, S or T; $P_2$ is G, P, A, V, L, I M, C, R, Y, W, H, K, R, Q, N, E, D, S or T; $P_3$ is G, P, A, V, L, I M, C, R, Y, W, H, K, R, Q, N, E, D, S or T; $P_4$ is G, P, A, V, L, I M, C, R, Y, W, H, K, R, Q, N, E, D, S or T; $P_5$ is G, P, A, V, L, I M, C, R, Y, W, H, K, R, Q, N, E, D, S or T; $P_6$ is G, P, A, V, L, I M, C, R, Y, W, H, K, R, Q, N, E, D, S, T or no amino acid; $P_7$ is G, P, A, V, L, I M, C, R, Y, W, H, K, R, Q, N, E, D, S, T or no amino acid; $P_8$ is G, P, A, V, L, I M, C, R, Y, W, H, K, R, Q, N, E, D, S, T or no amino acid; $P_9$ is G, P, A, V, L, I M, C, R, Y, W, H, K, R, Q, N, E, D, S, T or no amino acid; $P_{10}$ is G, P, A, V, L, I M, C, R, Y, W, H, K, R, Q, N, E, D, S, T or no amino acid; $P_{11}$ is G, P, A, V, L, I M, C, R, Y, W, H, K, R, Q, N, E, D, S, T or no amino acid; $P_{12}$ is G, P, A, V, L, I M, C, R, Y, W, H, K, R, Q, N, E, D, S, T or no amino acid; $P_{13}$ is G, P, A, V, L, I M, C, R, Y, W, H, K, R, Q, N, E, D, S, T or no amino acid; $P_{14}$ is G, P, A, V, L, I M, C, R, Y, W, H, K, R, Q, N, E, D, S, T or no amino acid; $P_{15}$ is G, P, A, V, L, I M, C, R, Y, W, H, K, R, Q, N, E, D, S, T or no amino acid; $P_{16}$ is G, P, A, V, L, I M, C, R, Y, W, H, K, R, Q, N, E, D, S, T or no amino acid; $P_{17}$ is G, P, A, V, L, I M, C, R, Y, W, H, K, R, Q, N, E, D, S, T or no amino acid; $P_{18}$ is G, P, A, V, L, I M, C, R, Y, W, H, K, R, Q, N, E, D, S, T or no amino acid; $P_{19}$ is G, P, A, V, L, I M, C, R, Y, W, H, K, R, Q, N, E, D, S, T or no amino acid; $P_{20}$ is G, P, A, V, L, I M, C, R, Y, W, H, K, R, Q, N, E, D, S, T or no amino acid; $P_{21}$ is G, P, A, V, L, I M, C, R, Y, W, H, K, R, Q, N, E, D, S, T or no amino acid; $P_{22}$ is G, P, A, V, L, I M, C, R, Y, W, H, K, R, Q, N, E, D, S, T or no amino acid; $P_{23}$ is G, P, A, V, L, I M, C, R, Y, W, H, K, R, Q, N, E, D, S, T or no amino acid; $P_{24}$ is G, P, A, V, L, I M, C, R, Y, W, H, K, R, Q, N, E, D, S, T or no amino acid; $P_{25}$ is G, P, A, V, L, I M, C, R, Y, W, H, K, R, Q, N, E, D, S, T or no amino acid.

"Oligosaccharide" refers to refers to a short chain of monosaccharides. Oligosaccharides typically include between about 2 and about 25 monosaccharides. A nonlimiting, generalized structure for oligosaccharides is shown below:

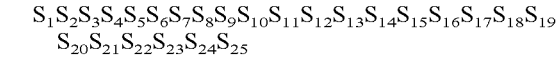

where $S_1$ is glucose, fructose, glucopyranose, ribitol, gluconic acid, glucosamine, or N-acetylneuraminide; $S_2$ is glucose, fructose, glucopyranose, ribitol, gluconic acid, glucosamine, or N-acetylneuraminide; $S_3$ is glucose, fructose, glucopyranose, ribitol, gluconic acid, glucosamine, N-acetylneuraminide or no monosaccharide; $S_4$ is glucose, fructose, glucopyranose, ribitol, gluconic acid, glucosamine, N-acetylneuraminide or no monosaccharide; $S_5$ is glucose, fructose, glucopyranose, ribitol, gluconic acid, glucosamine, N-acetylneuraminide or no monosaccharide; $S_6$ is glucose, fructose, glucopyranose, ribitol, gluconic acid, glucosamine, N-acetylneuraminide or no monosaccharide; $S_7$ is glucose, fructose, glucopyranose, ribitol, gluconic acid, glucosamine, N-acetylneuraminide or no monosaccharide; $S_8$ is glucose, fructose, glucopyranose, ribitol, gluconic acid, glucosamine, N-acetylneuraminide or no monosaccharide; $S_9$ is glucose, fructose, glucopyranose, ribitol, gluconic acid, glucosamine, N-acetylneuraminide or no monosaccharide; $S_{10}$ is glucose, fructose, glucopyranose, ribitol, gluconic acid, glucosamine, N-acetylneuraminide or no monosaccharide; $S_{11}$ is glucose, fructose, glucopyranose, ribitol, gluconic acid, glucosamine, N-acetylneuraminide or no monosaccharide; $S_{12}$ is glucose, fructose, glucopyranose, ribitol, gluconic acid, glucosamine, N-acetylneuraminide or no monosaccharide; $S_{13}$ is glucose, fructose, glucopyranose, ribitol, gluconic acid, glucosamine, N-acetylneuraminide or no monosaccharide; $S_{14}$ is glucose, fructose, glucopyranose, ribitol, gluconic acid, glucosamine, N-acetylneuraminide or no monosaccharide; $S_{15}$ is glucose, fructose, glucopyranose, ribitol, gluconic acid, glucosamine, N-acetylneuraminide or no monosaccharide; $S_{16}$ is glucose, fructose, glucopyranose, ribitol, gluconic acid, glucosamine, N-acetylneuraminide or no monosaccharide; $S_{17}$ is glucose, fructose, glucopyranose, ribitol, gluconic acid, glucosamine, N-acetylneuraminide or no monosaccharide; $S_{18}$ is glucose, fructose, glucopyranose, ribitol, gluconic acid, glucosamine, N-acetylneuraminide or no monosaccharide; $S_{19}$ is glucose, fructose, glucopyranose, ribitol, gluconic acid, glucosamine, N-acetylneuraminide or no monosaccharide; $S_{20}$ is glucose, fructose, glucopyranose, ribitol, gluconic acid, glucosamine, N-acetylneuraminide or no monosaccharide; $S_{21}$ is glucose, fructose, glucopyranose, ribitol, gluconic acid, glucosamine, N-acetylneuraminide or no monosaccharide; $S_{22}$ is glucose, fructose, glucopyranose, ribitol, gluconic acid, glucosamine, N-acetylneuraminide or no monosaccharide; $S_{23}$ is glucose, fructose, glucopyranose, ribitol, gluconic acid, glucosamine, N-acetylneuraminide or no monosaccharide; $S_{24}$ is glucose, fructose, glucopyranose, ribitol, gluconic acid, glucosamine, N-acetylneuraminide or no monosaccharide; $S_{25}$ is glucose, fructose, glucopyranose, ribitol, gluconic acid, glucosamine, N-acetylneuraminide or no monosaccharide.

"Organic molecule" refers to a molecule that includes carbon. Nonlimiting examples of organic molecules include: antibodies, antibody fragments, aptamers, oligonucleotides, oligopeptides, oligosaccharides, polynucleotides, polypeptides, polysaccharides, proteins, small molecule therapeutics, and large molecule therapeutics.

"Polynucleotide" refers to a single-stranded DNA or RNA molecule containing two or more nucleotides.

"Polypeptide" refers to a chain of two or more amino acids.

"Polysaccharide" refers to a chain or two or more monosaccharides.

"Protein" refers to a molecule made up of amino acids, typically long chains. A protein is usually necessary for a biological function and encoded by a gene within an organism. Classes of proteins include: structural proteins, storage proteins, defensive proteins, transport proteins, signal proteins, contractile proteins, and enzymes. Nonlimiting examples of proteins include: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1b; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab; DNA polymerase.

"Small molecule therapeutic" refers to an organic molecule of molecular weight less than 1000 g/mol, where the molecule has been, or is currently, used for a clinical application. Nonlimiting examples of small molecule therapeutic classes include: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-glucosidase inhibitors; alternative medicines; amebicides; aminoglycosides; aminopenicillins; aminosalicylates; AMPA receptor antagonists; amylin analogs; analgesics; androgens and anabolic steroids; angiotensin converting enzyme inhibitors; angiotensin II inhibitors; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiarrheals; antidiuretic hormones; antiemetic/antivertigo agents; antifungals; antigonadotropic agents; antigout agents; antihistamines; antihyperlipidemic agents; antihyperuricemic agents; antimalarial agents; antimalarial combinations; antimalarial quinolines; antimetabolites; antimigraine agents; antineoplastic detoxifying agents; antineoplastic interferons; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; bisphosphonates; bone resorption inhibitors; bronchodilators; calcineurin inhibitors; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD30 monoclonal antibodies; CD33 monoclonal antibodies; CD52 monoclonal antibodies; central nervous system agents; cephalosporins; cerumenolytics; CFTR potentiators; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; dibenzazepine anticonvulsants; digestive enzymes; dipeptidyl peptidase 4 inhibitors; diuretics; dopaminergic antiparkinsonism agents; echinocandins; EGFR inhibitors; estrogen receptor antagonists; estrogens; factor Xa inhibitors; fatty acid derivative anticonvulsants; fibric acid derivatives; first generation cephalosporins; fourth generation cephalosporins; gamma-aminobutyric acid analogs; gamma-aminobutyric acid reuptake inhibitors; gastrointestinal agents; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; guanylate cyclase-C agonists; *H. pylori* eradication agents; H2 antagonists; hedgehog pathway inhibitorshematopoietic stem cell mobilizer; heparin antagonists; heparins; HER2 inhibitors; histone deacetylase inhibitors; hormones; hormones/antineoplastics; hydantoin anticonvulsants; hydrazide derivatives; immune globulins; immunologic agents; immunostimulants; immunosuppressive agents; incretin mimetics; inotropic agents; insulin; insulin-like growth factor; integrase strand transfer inhibitor; interferons; interleukin inhibitors; interleukins; ketolides; leprostatics; leukotriene modifiers; lincomycin derivatives; loop diuretics; lymphatic staining agents; lysosomal enzymes; macrolide derivatives; macrolides; mast cell stabilizers; meglitinides; metabolic agents; methylxanthines; mineralocorticoids; mitotic inhibitors; monoamine oxidase inhibitors; mTOR inhibitors; mucolytics; multikinase inhibitors; muscle relaxants; mydriatics; narcotic analgesics; natural penicillins; neuraminidase inhibitors; neuromuscular blocking agents; neuronal potassium channel openers; next generation cephalosporins; nicotinic acid derivatives; NNRTIs; non-cardioselective beta blockers; non-sulfonylureas; nonsteroidal anti-inflammatory agents; nucleoside reverse transcriptase inhibitors (NRTIs); oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proteasome inhibitors; proton pump inhibitors; psoralens; psychotherapeutic agents; purine nucleosides; pyrrolidine anticonvulsants; quinolones; recombinant human erythropoietins; renin inhibitors; respiratory agents; rifamycin derivatives; salicylates; sclerosing agents; second generation cephalosporins; selective estrogen receptor modulators; selective immunosuppressants; selective phosphodiesterase-4 inhibitors; selective serotonin reuptake inhibitors; serotonin-norepinephrine reuptake inhibitors; serotoninergic neuroenteric modulators; sex hormone combinations; sex hormones; SGLT-2 inhibitors; skeletal muscle relaxants; smoking cessation agents; somatostatin and somatostatin analogs; statins; *streptomyces* derivatives; succinimide anticonvulsants; sulfonamides; sulfonylureas; synthetic ovulation stimulants; tetracyclic antidepressants; tetracyclines; therapeutic radiopharmaceuticals; therapeutic vaccines; thiazide diuretics; thiazolidinediones; thioxanthenes; third generation cephalosporins; thrombin inhibitors; thrombolytics; thyroid drugs; TNF alfa inhibitors; tocolytic agents; triazine anticonvulsants; tricyclic antidepressants; trifunctional monoclonal antibodies; urea anticonvulsants; urea cycle disorder agents; urinary anti-infectives; urinary antispasmodics; vasodilators; vasopressin antagonists; vasopressors; VEGF/VEGFR inhibitors; viral vaccines.

"Small organic molecule" refers to an organic molecule of molecular weight less than 1000 g/mol.

"Supporting substrate" refers to a second, different substrate onto which the graphene substrate can be adhered. Nonlimiting examples of such substrates include: organic polymers, metals, crystalline inorganic materials, non-crystalline inorganic materials, and ceramics.

"Van der Waals interaction" refers to the sum of the attractive forces between two molecules other than those due to covalent bonds, ionic bonds or hydrogen bonds. The strength of a Van der Waals interaction typically ranges from approximately 1 kcal/mol to approximately 2 kcal/mol.

The present invention relates to the internal (i.e., non-edge) functionalization of graphene substrates such as the one shown in FIG. 1. The referenced substrate (100) includes non-edge regions (110) and edge regions (120).

Figure 2:
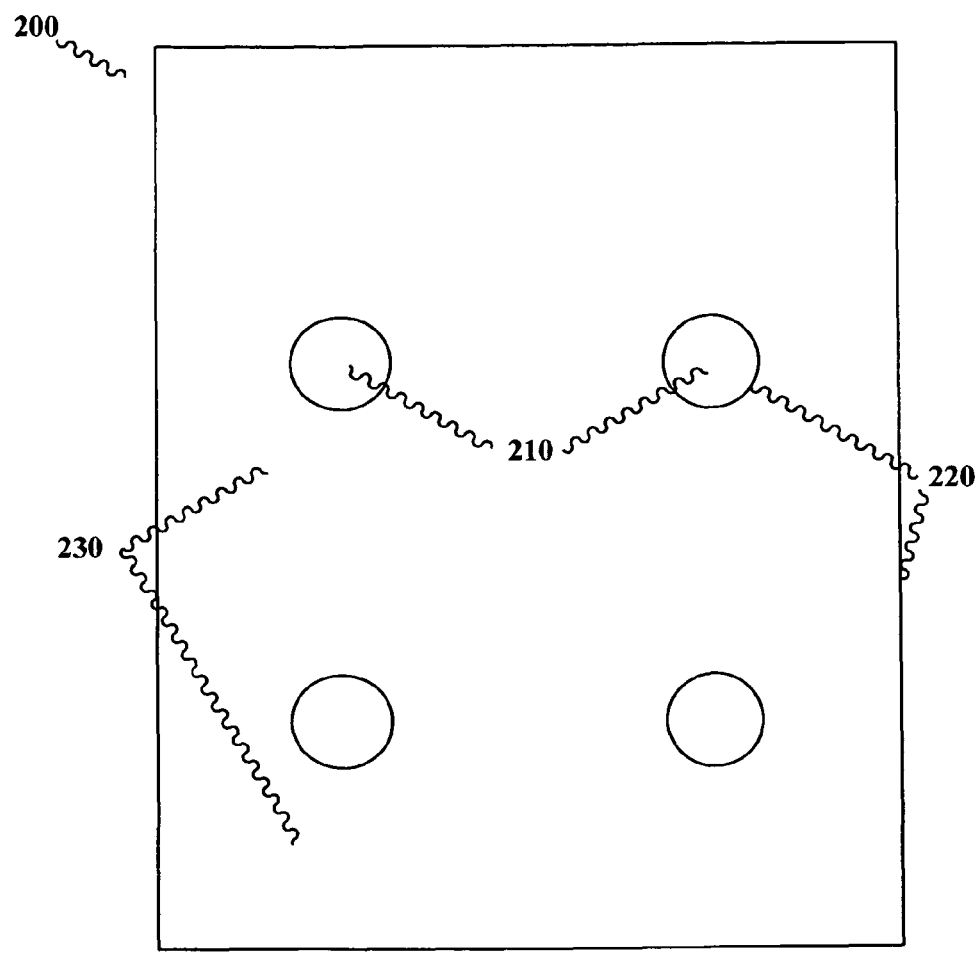
FIG. 2 is an illustration of a graphene substrate (200) having holes (210) where there is no graphene, edge regions (220) and non-edge regions (230).
Figure 3:
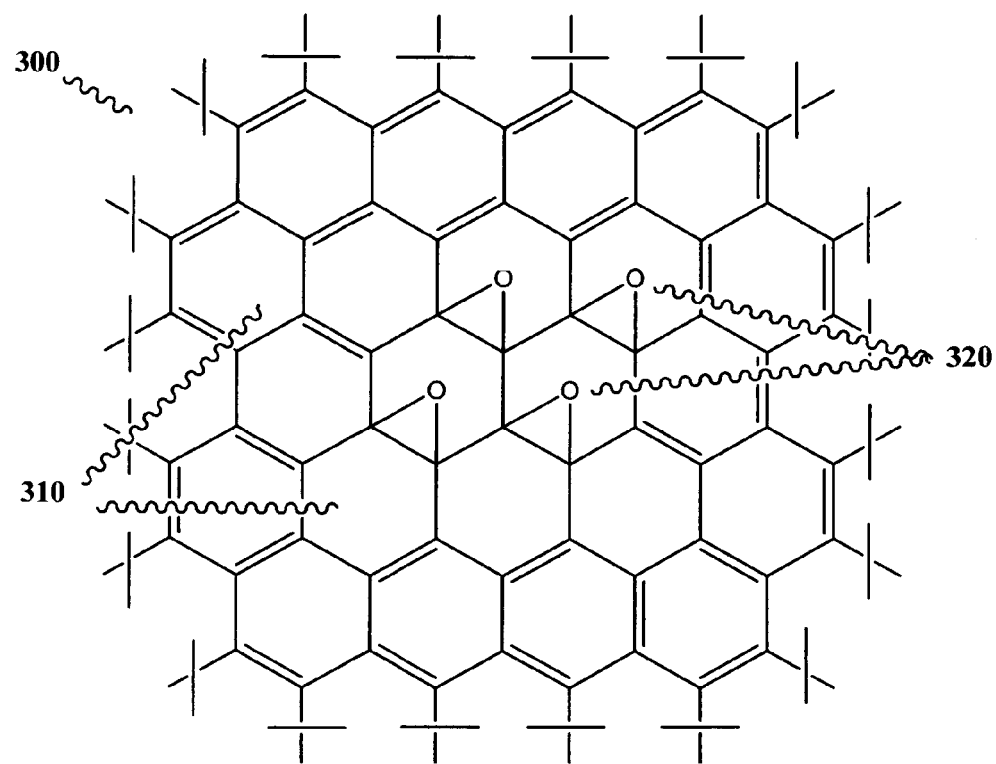
FIG. 3 is an illustration of a portion of a graphene substrate (300) having non-edge regions (310) and epoxy groups (320) within the non-edge regions.
Figure 4:
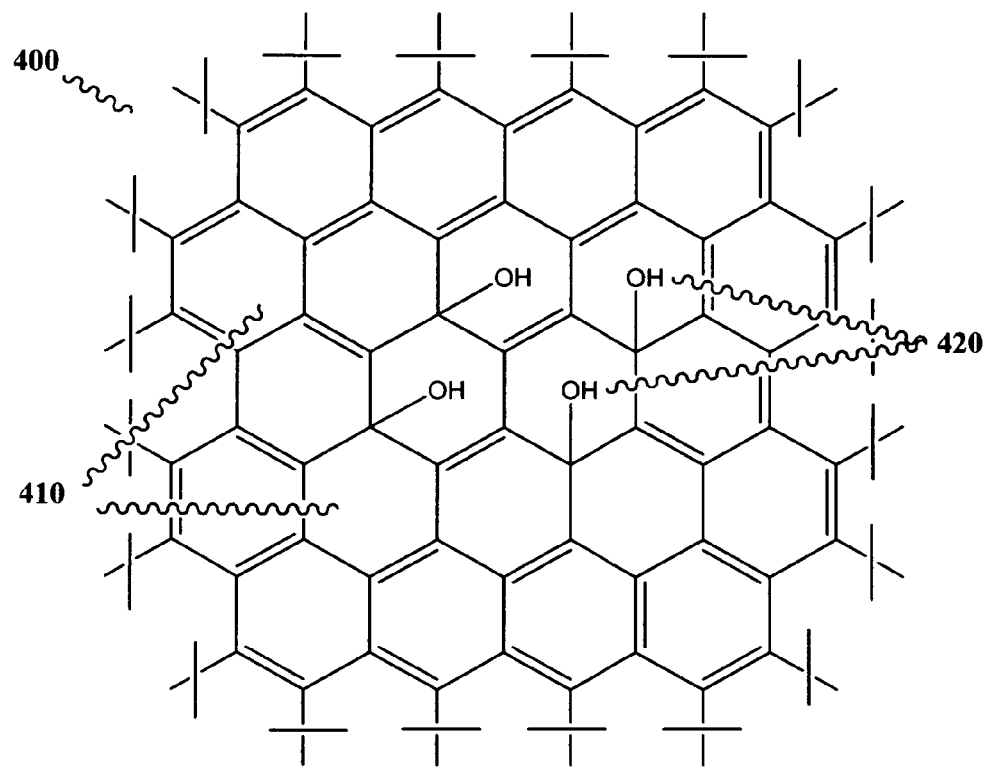
FIG. 4 is an illustration of a portion of a graphene substrate (400) having non-edge regions (410) and hydroxyl groups (420) within the non-edge regions.

FIG. 2 shows another graphene substrate. The referenced substrate (200) includes holes (210), edge regions (220) and non-edge regions (230). One embodiment of such a graphene substrate is graphene nanomesh. FIG. 3 shows a portion of a graphene substrate (300). The substrate includes non-edge regions (310) and epoxy moieties (320) within the non-edge regions. FIG. 4 shows a portion of a graphene substrate (400). The substrate includes non-edge regions (410) and hydroxyl moieties (420) within the non-edge regions.

Figure 5:
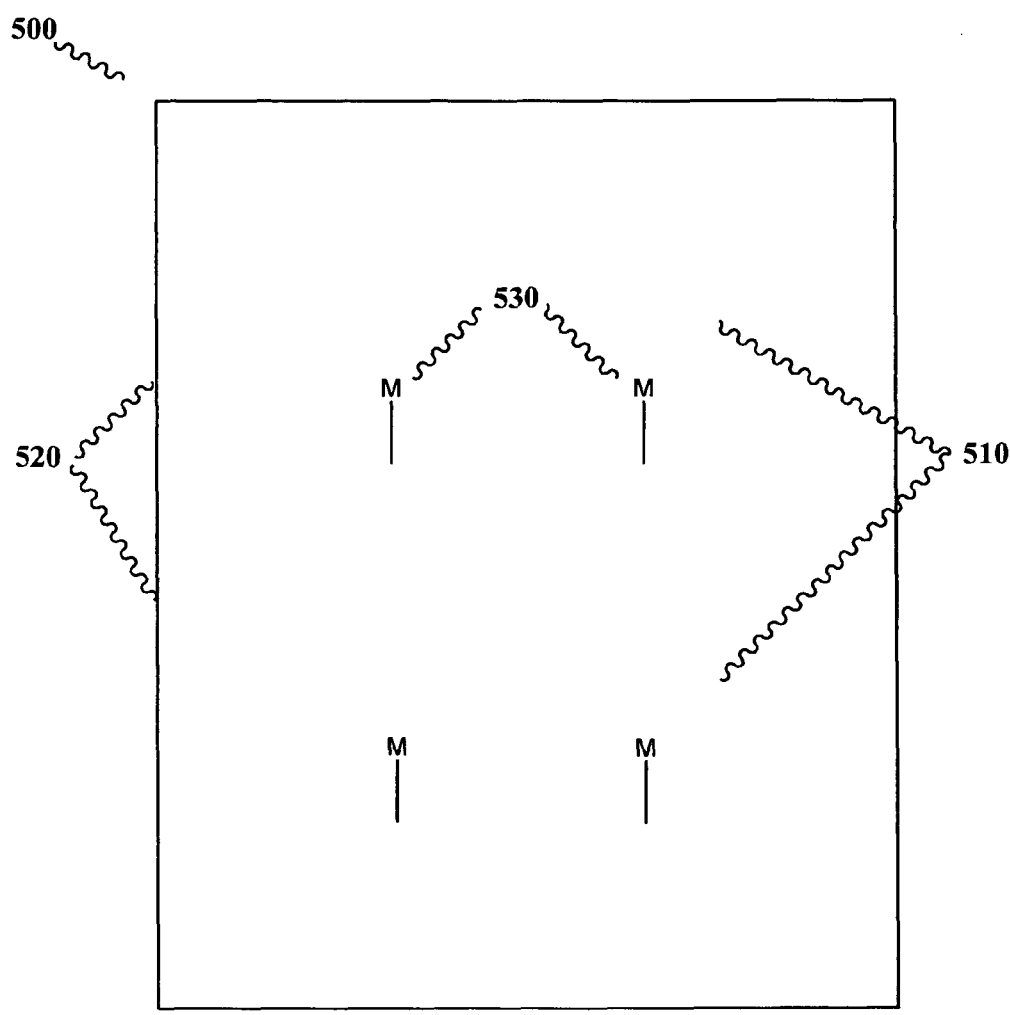
FIG. 5 is an illustration of a graphene substrate (500) having non-edge regions (510) and edge regions (520), and where the non-edge regions are functionalized with one or more molecules (M, 530).
Figure 6:
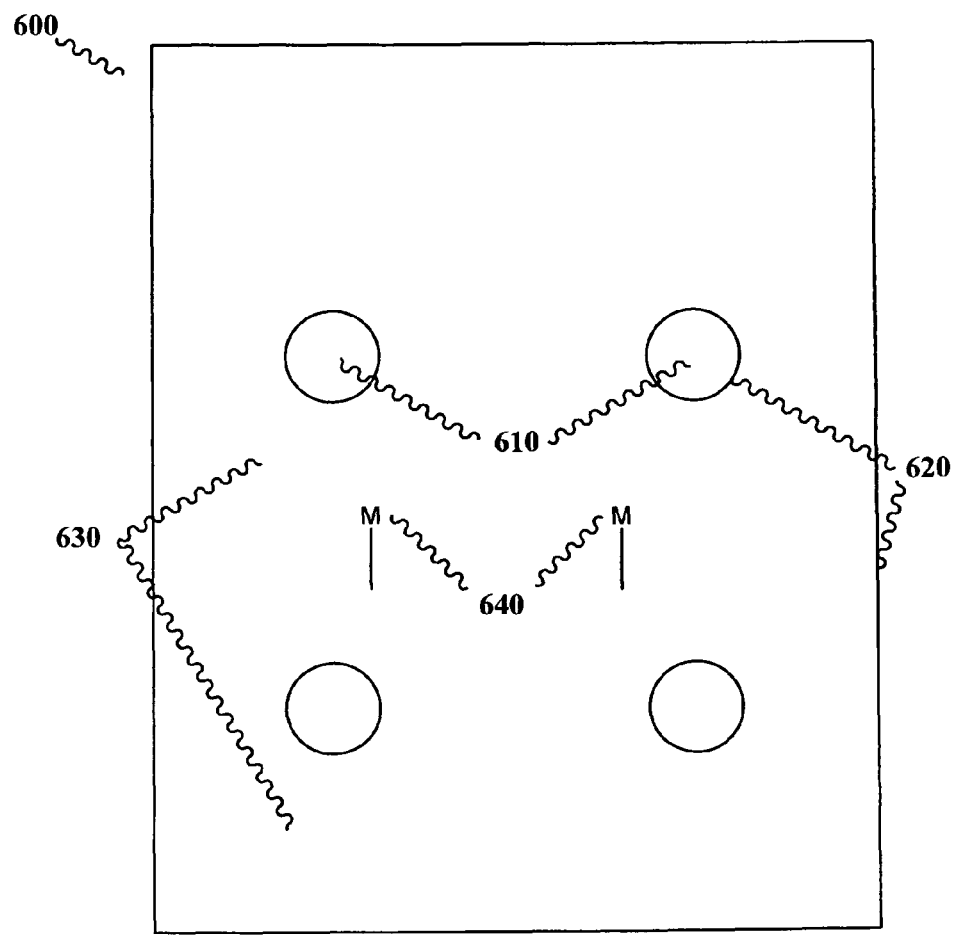
FIG. 6 is an illustration of a graphene substrate (600) having edge regions (620) and non-edge regions (630), as well as holes (610) where there is no graphene, and where the non-edge regions are functionalized with one or more molecules (M, 640).

In a composition aspect, the present invention is directed to internally functionalized graphene substrates. FIG. 5 is an illustration of a graphene substrate (500) having non-edge (510) and edge (520) regions, where the non-edge regions are functionalized with one or more molecules (M, 530). The functionalization typically occurs through addition of nucleophilic molecules to epoxy moieties on the graphene surface or electrophilic molecules to hydroxyl moieties on the graphene surface. FIG. 6 is an illustration of a graphene substrate (600) having edge (620) and non-edge regions (630), as well as holes (610) where there is no graphene, and where the non-edge regions are functionalized with one or more molecules (M, 640).

Figure 7:
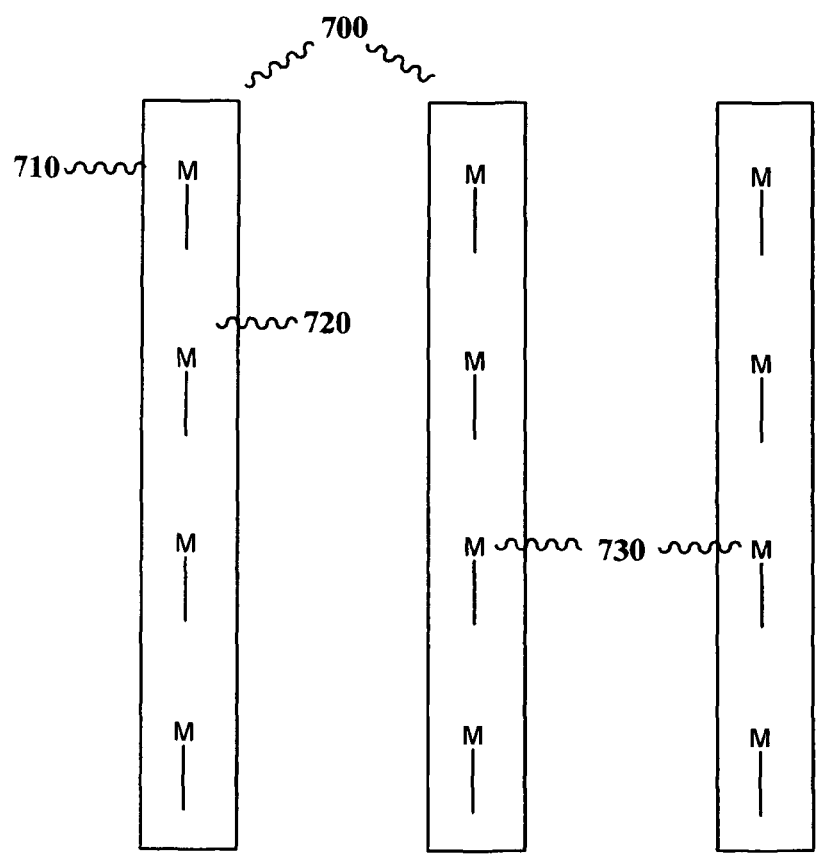
FIG. 7 is an illustration of three ribbons (700) of graphene substrates that have edge regions (710), non-edge regions (720), and where the non-edge regions are functionalized with one or more molecules (M, 730).
Figure 8:
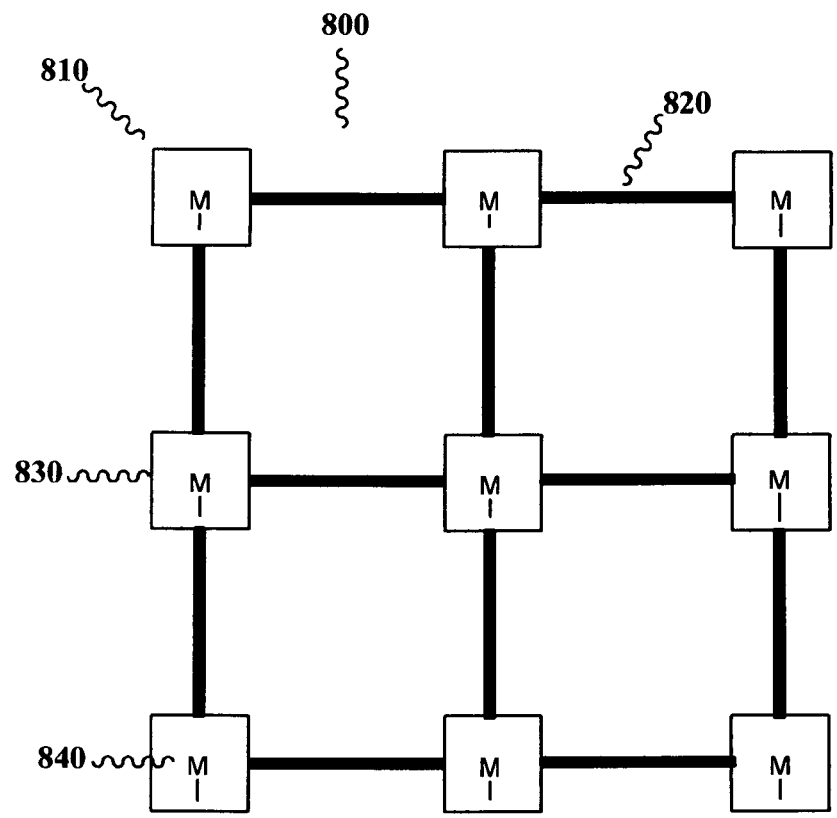
FIG. 8 is an illustration of system (800) of interconnected graphene substrates (810), where the graphene substrates have edge regions (830) and non-edge regions that are functionalized with one or more molecules (M, 840), and where the graphene substrates are connected with electrically conducting 4 units (820).

Although a rectangular graphene substrate is shown in various figures, any suitable graphene substrate can be used. For instance, FIG. 7 is an illustration of three ribbons (700) of graphene substrates that have edge regions (710) and non-edge regions (720), where the non-edge regions are functionalized with one or more molecules (M, 730). FIG. 8 shows a system (800) of interconnected graphene substrates (810). The substrates have edge (830) and non-edge regions (840), and the non-edge regions are functionalized with one or more molecules (M). The substrates are further connected with electrically conducting units (820).

Figure 9:
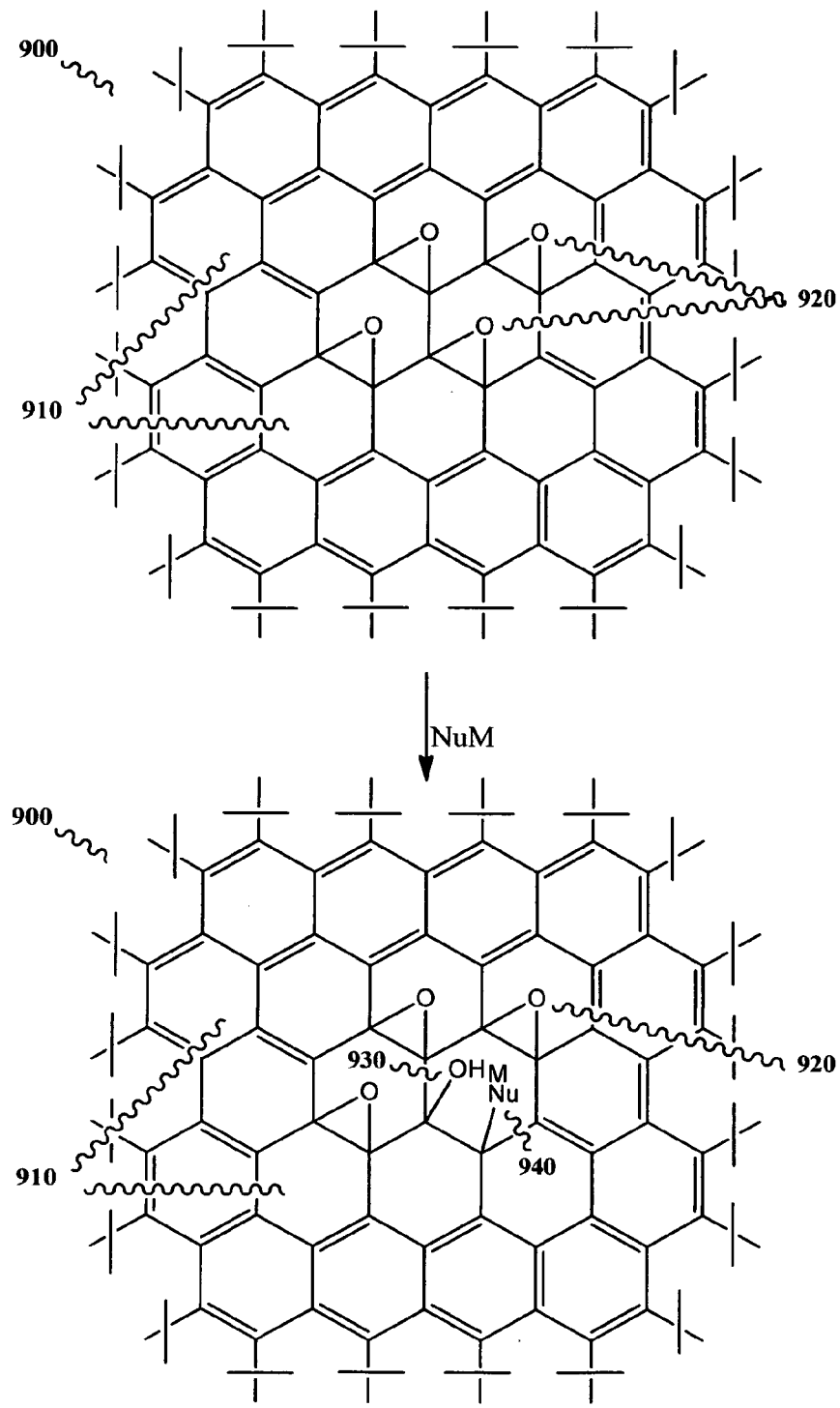
FIG. 9 is an illustration of the functionalization of epoxy groups (920) on non-edge regions (910) of a portion of a graphene substrate (900) through reaction with a molecule NuM, where "Nu" is a nucleophilic moiety and "M" is an attached organic or inorganic moiety, to provide a functionalized group (940) and a hydroxyl group (930).

FIG. 9 is an illustration of the functionalization of a portion of a graphene substrate (900) through reaction of an epoxy group (920), within a non-edge region (910) of the substrate, with a molecule NuM, where "Nu" is a nucleophilic moiety and "M" is an attached organic or inorganic moiety, to provide the functionalized group (940). "Nu" is any suitable nucleophilic moiety. Nonlimiting examples include $NH_2$-M (amine formation), HO-M (ether formation), HS-M (thioether formation). "M" is any suitable organic or inorganic moiety. Nonlimiting examples include $NH_2$-protein—where the $NH_2$ group ("Nu") is part of the native protein or the termination of a linking group attached to the protein—$NH_2$-oligopeptide—where the $NH_2$ group is part of the oligopeptide (e.g., termination of sidechain) or the termination of a linking group attached to the protein—$NH_2$-oligonucleotide—where the $NH_2$ group is the termination of a linking group attached to the oligonucleotide—$NH_2$-oligosaccharide—where the $NH_2$ group is the termination of a linking group attached to the oligonucleotide—$NH_2$-antibody—where the $NH_2$ group is part of the antibody or the termination of a linking group attached to the antibody—$NH_2$—[antibody fragment]—where the $NH_2$ group is part of the antibody fragment or the termination of a linking group attached to the antibody fragment—$NH_2$-aptamer—where the $NH_2$ group is the termination of a linking group attached to the aptamer—$NH_2$—[inorganic molecule]—where the $NH_2$ group is the termination of a linking group attached to the inorganic molecule—$NH_2$—[large molecule therapeutic]—where the $NH_2$ group is part of the large molecule therapeutic or the termination of a linking group attached to the large molecule therapeutic—$NH_2$—[organic molecule]—where the $NH_2$ group is part of the organic molecule or the termination of a linking group attached to the organic molecule—$NH_2$—[small molecule therapeutic]—where the $NH_2$ group is part of the small molecule therapeutic or the termination of a linking group attached to the small molecule therapeutic.

Figure 10:
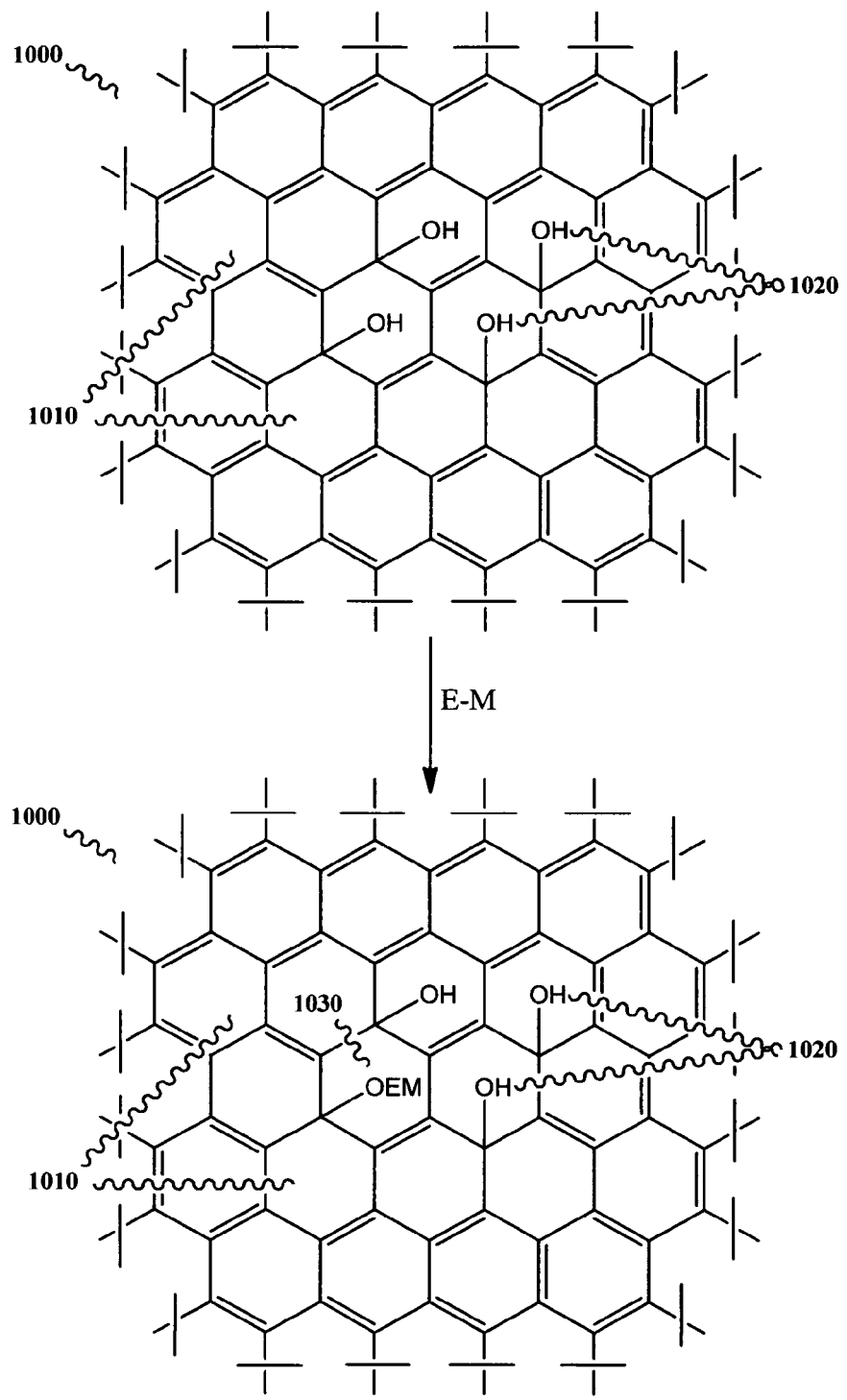
FIG. 10 is an illustration of the functionalization of hydroxyl groups (1020) on non-edge regions (1010) of a portion of a graphene substrate (1000) through reaction with a molecule EM, where "E" is an electrophilic moiety and "M" is an attached organic or inorganic moiety, to provide a functionalized group (1030).

FIG. 10 is an illustration of the functionalization of hydroxyl groups (1020) within non-edge regions (1010) of a portion of a graphene substrate, where "E" is an electrophilic moiety and "M" is an attached organic or inorganic moiety, to provide the functionalized group 1030. Such reactions are typically base catalyzed. "E" is any suitable electrophilic group. Nonlimiting examples include Cl—C(O)M (ester formation), $ICH_2M$ (ether formation), Cl—C(O)OM (carbonate formation), $CH_2CHC(O)M$ (ether formation), OCNM (carbamate formation). "M" is any suitable organic or inorganic moiety. Nonlimiting examples of EMs include: OCN-protein—where the "N" atom is part of the native protein of the termination of a linking group attached to the protein—OCN-oligopeptide—where the "N" atom is part of the oligopeptide (e.g., termination of sidechain) or the termination of a linking group attached to the oligopeptide—OCN-oligonucleotide—where the "N" atom is the termination of a linking group attached to the oligonucleotide—OCN-oligosaccharide—where the "N" atom is the termination of a linking group attached to the oligosaccharide—OCN-antibody—where the "N" atom is part of the antibody of the termination of a linking group attached to the antibody—OCN—[antibody fragment]—where the "N" atom is part of the antibody fragment or the termination of a liking group attached to the antibody fragment—OCN-aptamer—where the "N" atom is the termination of a linking group attached to the aptamer—OCN—[inorganic molecule]—where the "N" atom is the termination of a linking group attached to the inorganic molecule—OCN—[large molecule therapeutic]—where the "N" atom is part of the large molecule therapeutic or the termination of a linking group attached to the large molecule therapeutic—OCN—[organic molecule]—where the "N" atom is part of the organic molecule or the termination of a linking group attached to the organic molecule—OCN—[small molecule therapeutic]—where the "N" atom is part of the small molecule therapeutic or the termination of a linking group attached to the small molecule therapeutic.

Figure 11:
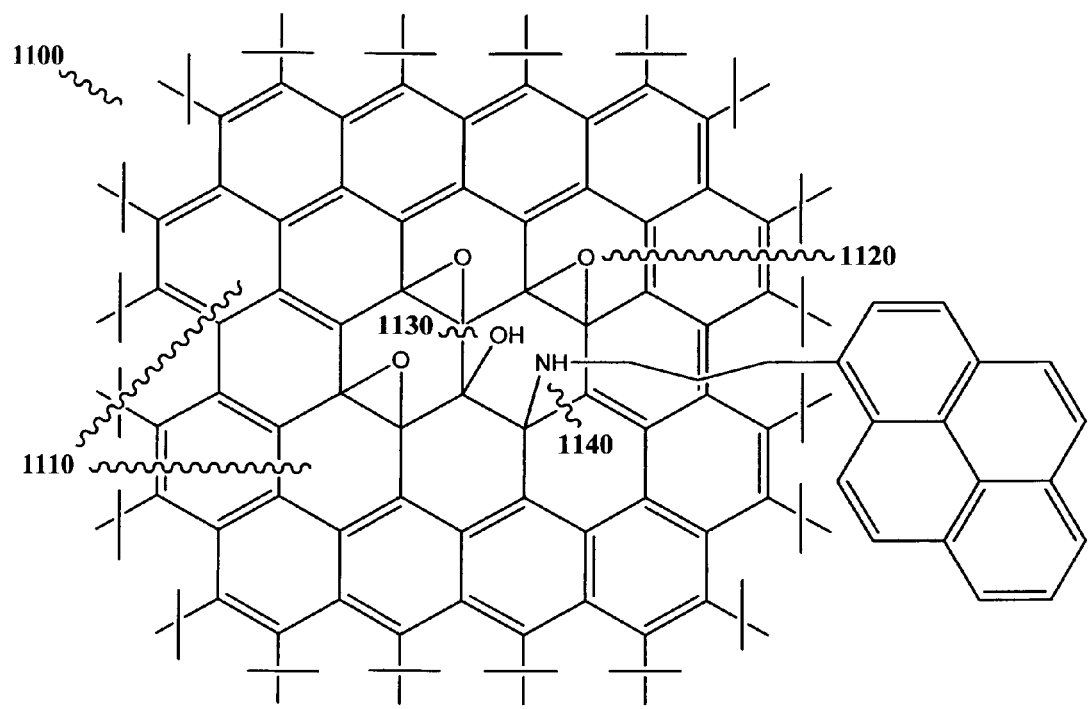
FIG. 11 is an illustration of a portion of a graphene substrate (1100) functionalized on a non-edge region (1110) with an amine including a pyrene moiety (1140) and having epoxy (1120) and hydroxy (1130) moieties.

FIG. 11 generally shows the functionalization of an epoxy moiety within a non-edge region of a portion of a graphene substrate with a Nu-M moiety that will promote pi-pi, non-covalent bonding with another aromatic pi system (e.g., pyrene containing molecule). Specifically, it shows an amine (1140) formed from opening of an epoxy moiety attached to a non-edge region (1110) of a portion of a graphene substrate (1100) where the NuM is $NH_2$—$(CH_2)_4$—$C_{15}H_9$.

Figure 12:
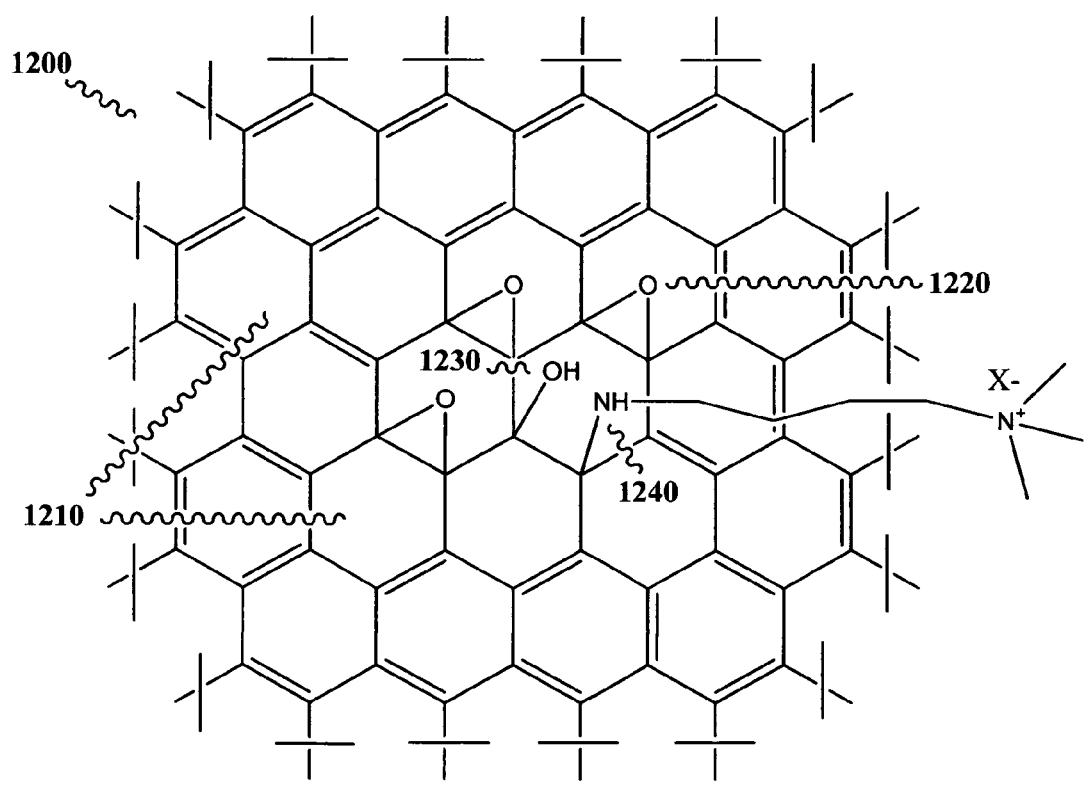
FIG. 12 is an illustration of a portion of a graphene substrate (1200) functionalized on a non-edge region (1210) with an amine including an ammonium ion (1240) and having epoxy (1220) and hydroxy (1230) moieties.

FIG. 12 generally shows the functionalization of an epoxy moiety within the non-edge region of a portion of a graphene substrate with a Nu-M moiety that will promote ionic bond formation with a negatively charged molecule. Specifically, it shows an amine (1240) formed from opening of an epoxy moiety attached to a non-edge region (1210) of a portion of a graphene substrate (1200) where the NuM is $NH_2$—$(CH_2)_5$—$N(CH_3)_3X$.

Figure 13:
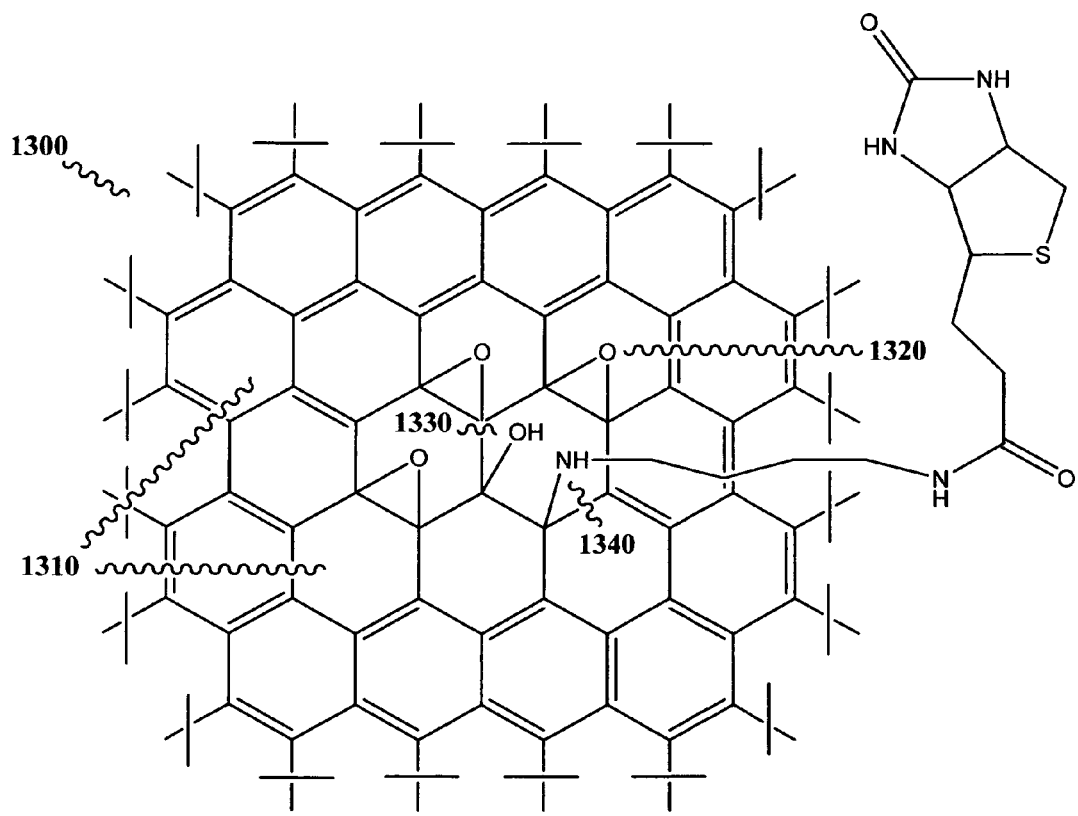
FIG. 13 is an illustration of a portion of a graphene substrate (1300) functionalized on a non-edge region (1310) with an amine including a biotin moiety (1340) and having epoxy (1320) and hydroxy (1330) moieties.

FIG. 13 generally shows the functionalization of an epoxy moiety within the non-edge region of a portion of a graphene substrate with a Nu-M moiety that will promote strong hydrogen bond formation. Specifically, it shows an amine (1340) formed from opening of an epoxy moiety attached to a non-edge region (1310) of a portion of a graphene substrate (1300) where the NuM is $NH_2$—$(CH_2)_4$—$NH(CO)$—$(CH_2)_3$—$C_5H_7N_2OS$ (biotin containing moiety).

Figure 14:
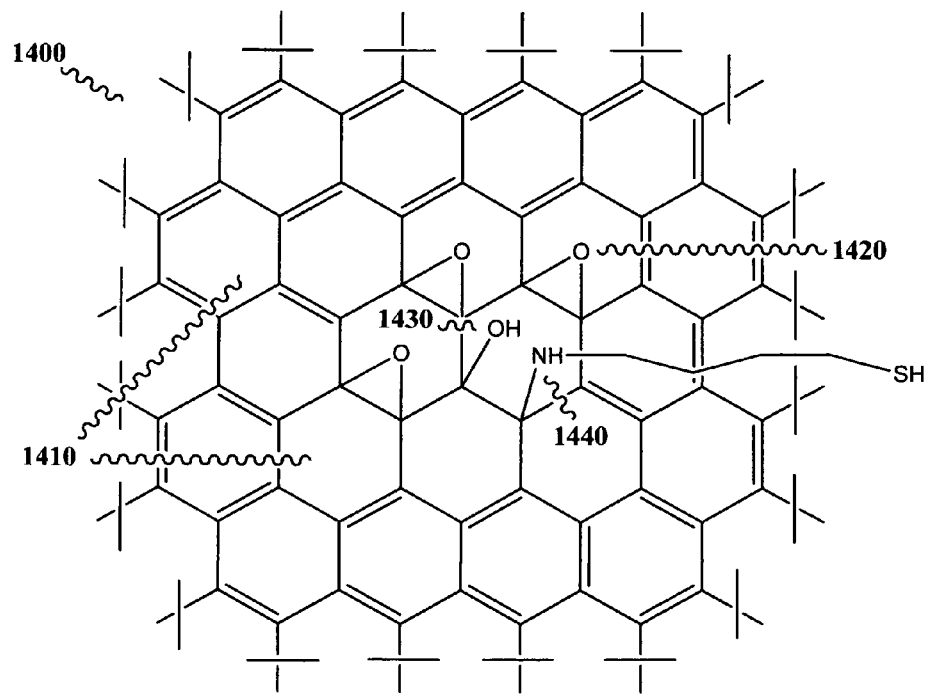
FIG. 14 is an illustration of a portion of a graphene substrate (1400) functionalized on a non-edge region (1410) with an amine including a thiol moiety (1440) and having epoxy (1420) and hydroxy (1430) moieties.

FIG. 14 generally shows the functionalization of an epoxy moiety within the non-edge region of a portion of a graphene substrate with a Nu-M moiety that will promote disulfide bond formation. Specifically, it shows an amine (1440) formed from opening of an epoxy moiety attached to a non-edge region (1410) of a portion of a graphene substrate (1400) where the NuM is $NH_2$—$(CH_2)_4$—SH.

Figure 15:
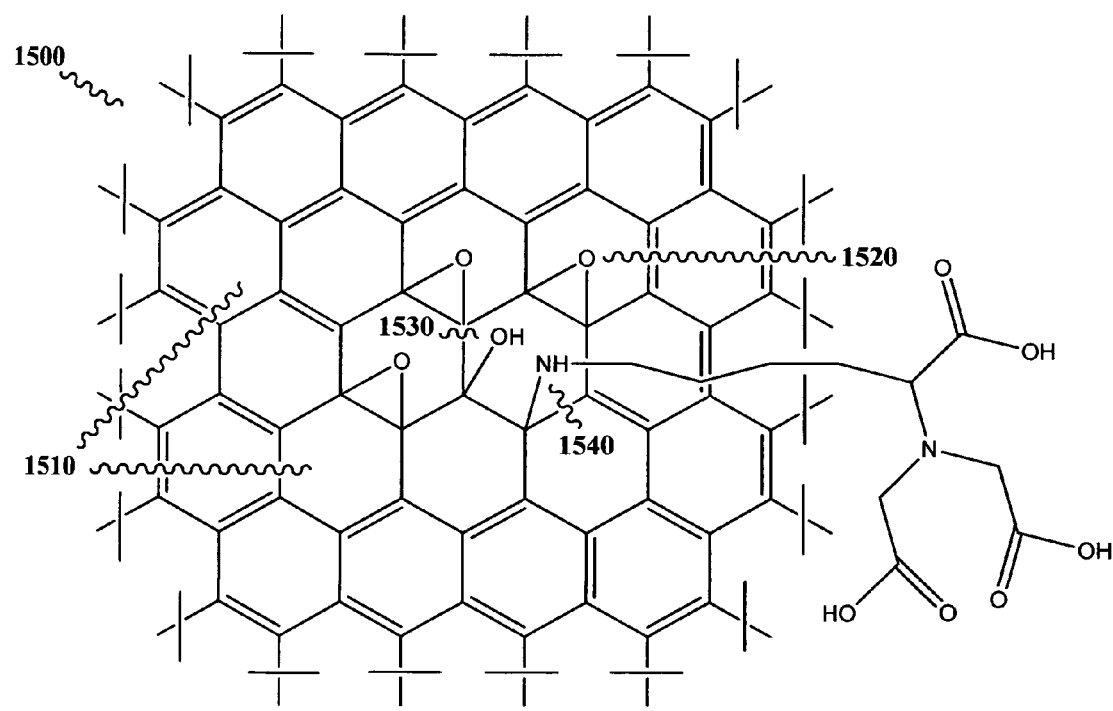
FIG. 15 is an illustration of a portion of a graphene substrate (1500) functionalized on a non-edge region (1510) with an amine including an amino triacetic acid moiety (1540) and having epoxy (1520) and hydroxy (1530) moieties.

FIG. 15 generally shows the functionalization of an epoxy moiety within the non-edge region of a portion of a graphene substrate with a Nu-M moiety that will promote binding to a metal. Specifically, it shows an amine (1540) formed from opening of an epoxy moiety attached to a non-edge region (1510) of a portion of a graphene substrate (1500) where the NuM is $NH_2$—$(CH_2)_4CH(CO_2H)(N(CH_2CO_2H)_2)$.

Figure 16:
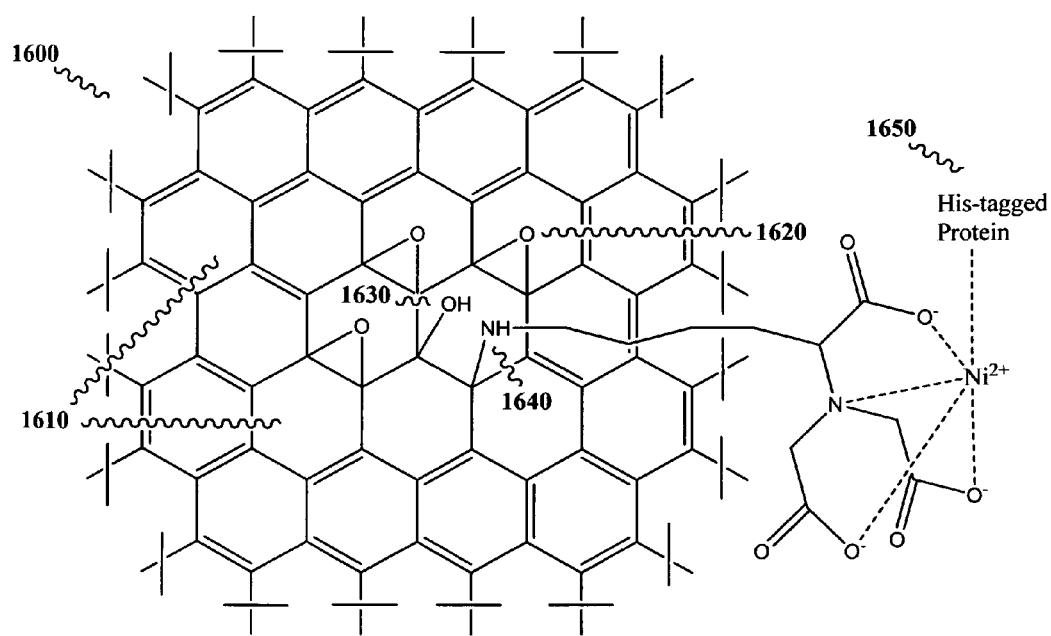
FIG. 16 is an illustration of a portion of a graphene substrate (1600) functionalized on a non-edge region (1610) with an amine including an amino triacetic acid bound to a nickel salt, which is in turn bound to a Histidine-tagged protein (1650). The substrate further includes epoxy (1620) and hydroxyl (1630) moieties.

FIG. 16 shows the binding of a $Ni^{2+}$ ion to the triacetic acid moiety (1640) attached to the non-edge regions (1610) of a portion of a graphene substrate (1600) originally shown in FIG. 15. FIG. 16 further shows the binding of a His-tagged protein (1650) to the bound $Ni^{2+}$ ion.

Any suitable functionalization chemistry may be used to functionalize a graphene substrate. The following are certain general conditions for functionalizing a graphene substrate with proteins and oligopeptides: The amine group (—$NH_2$) is the most common moiety used for attaching proteins to a graphene support. An amine group exists at the N-terminus of each polypeptide chain and in the side chain of certain amino acids (e.g., lysine). Nonlimiting examples of chemistries that can be used include: NHS ester-activation; aldehyde-activation; azlactone activation; and CDI activation.

Sulfhydryl groups on proteins (e.g., side chain of cysteine) may also be used to attach a protein to a graphene substrate. Nonlimiting examples of chemistries that can be used include: maleimide activation; iodoacetyl activation; and, pyridyl disulfide activation. Carboxyl groups on the proteins are also used to attach the molecules to a graphene substrate. EDC-mediated attachment is a typically used method.

General conditions for functionalizing a graphene substrate with oligonucleotides typically include amino, thiol or ACRYDITE™ modified oligonucleotides. An amino group can be attached to the 5' or 3' end of an oligonucleotide using standard chemistries. An amine modified oligonucleotide can be attached to a carboxyl group on the edge of a graphene substrate using carbodiimide, or other, reaction conditions. A thiol modifier can also be attached to the 5' or 3' end of an oligonucleotide. A thiol modified oligonucleotide can be attached to a graphene substrate, for example, by using maleimide, bromide, iodide or sulphonyl derivatives of the graphene edge region.

The following are general conditions for functionalizing a graphene substrate with oligosaccharides: formation of a hydrazide derivated using an activated carboxyl group on the edge region of the graphene substrate and subsequent reaction with an aldehyde moiety on the oligosaccharide.

Figure 17:
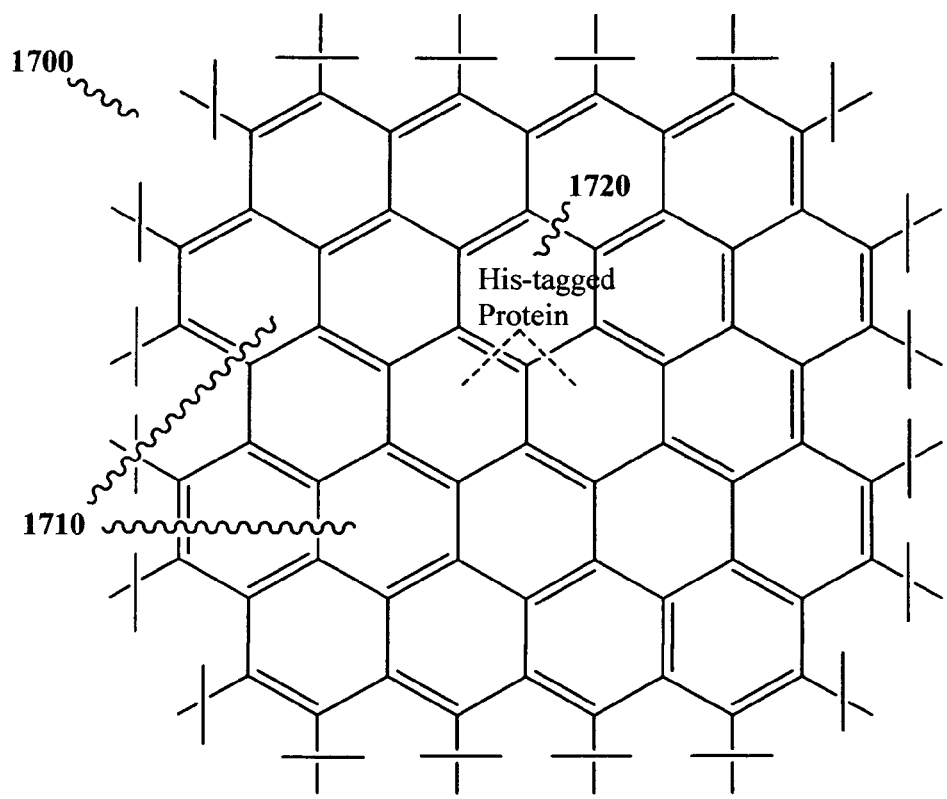
FIG. 17 is an illustration of a portion of a graphene substrate (1700) functionalized on a non-edge region (1710) through non-covalent association of a Histidine-tagged protein (1720) to its surface.
Figure 18:
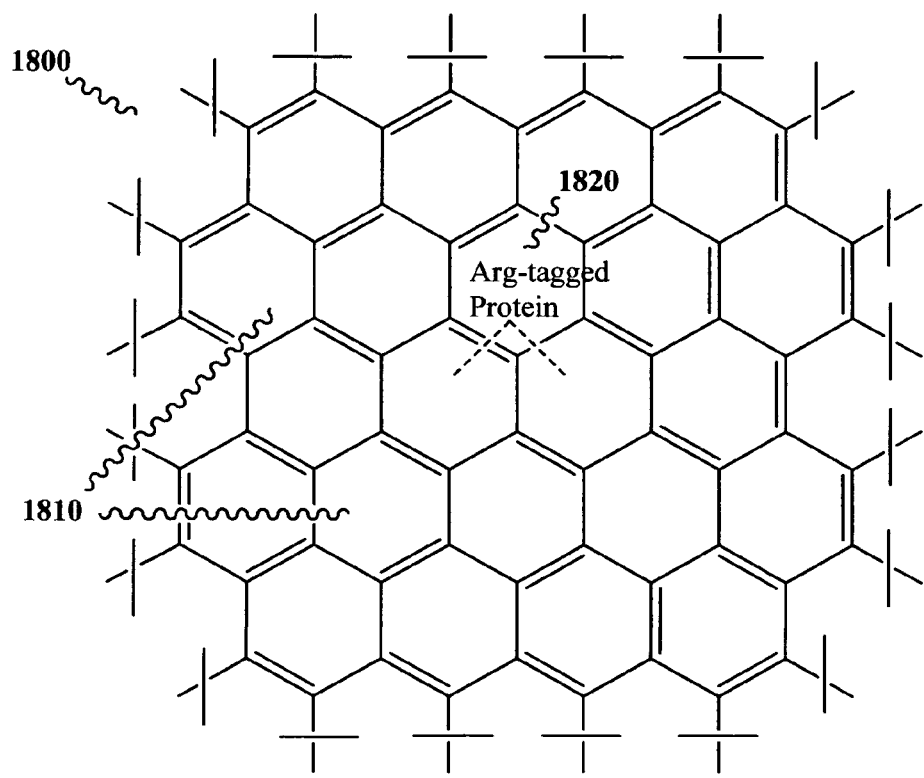
FIG. 18 is an illustration of a portion of a graphene substrate (1800) functionalized on a non-edge region (1810) through non-covalent association of an Arginine-tagged protein (1820) to its surface.
Figure 19:
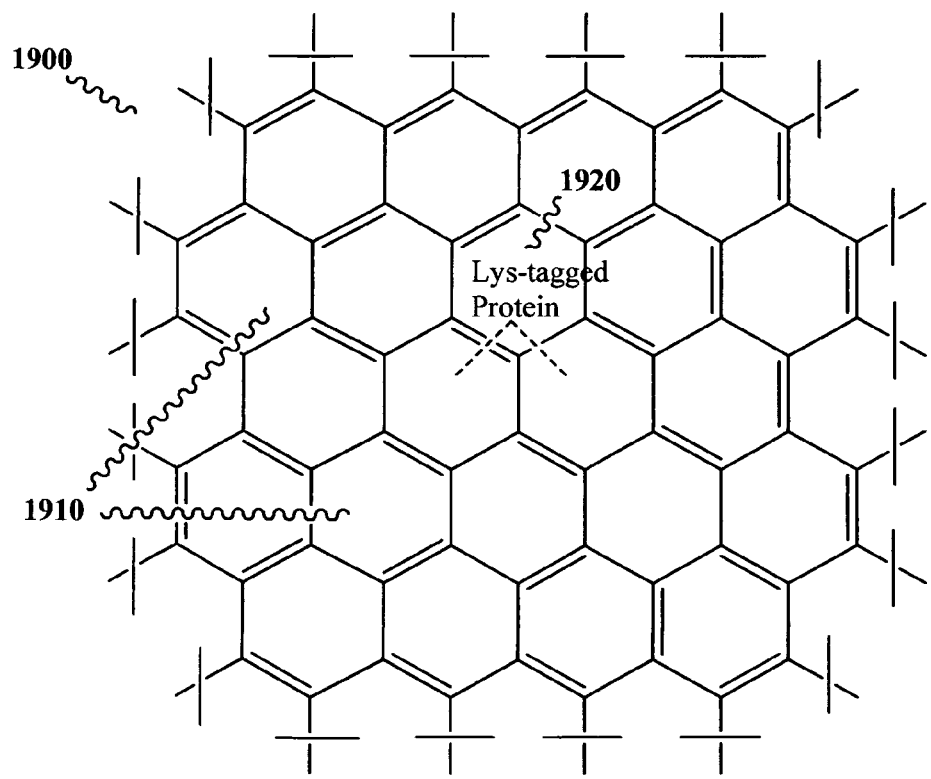
FIG. 19 is an illustration of a portion of a graphene substrate (1900) functionalized on a non-edge region (1910) through non-covalent association of a Lysine-tagged protein (1920) to its surface.
Figure 20:
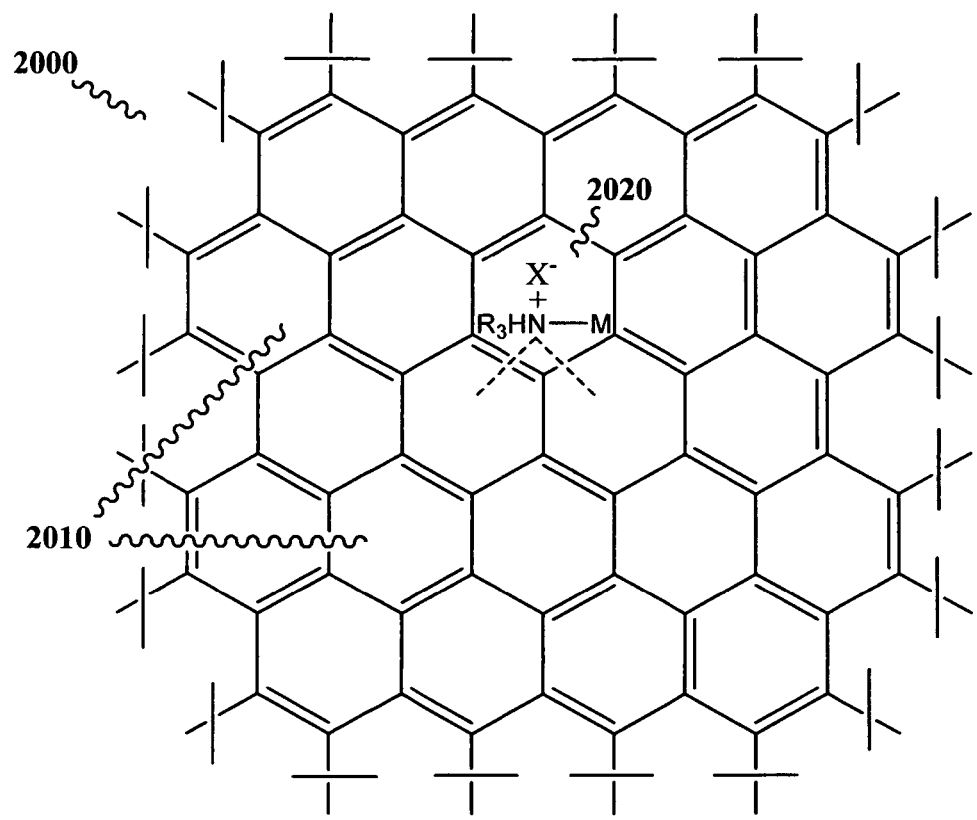
FIG. 20 is an illustration of a portion of a graphene substrate (2000) functionalized on a non-edge region (2010) through non-covalent association of a Cation-tagged molecule (2020) to its surface.

The present invention is furthermore directed to internal functionalization (i.e., non-edge regions) of graphene substrates through non-covalent binding. FIG. 17 shows the direct, non-covalent binding of His-tagged protein 1720 to non-edge regions (1710) of a portion of a graphene substrate (1700). FIG. 18 shows the direct, non-covalent binding of Arg-tagged protein 1820 to non-edge regions (1810) of a portion of a graphene substrate (1800). FIG. 19 shows the direct, non-covalent binding of Lys-tagged protein 1920 to non-edge regions (1910) of a portion of a graphene substrate (1900). FIG. 20 shows the direct, non-covalent binding of cation-tagged protein 2020 to non-edge regions (2010) of a portion of a graphene substrate (2000).

The functionalized graphene substrates of the present invention include attached molecules (M) at certain populations per unit area. The molecules are present on the substrates at a population of at least one molecule per 30,000 $nm^2$. In certain cases, the population is at least 1 molecule per 20,000 $nm^2$, at least 1 molecule per 10,000 $nm^2$, at least 1 molecule per 5,000 $nm^2$, at least 1 molecule per 4,000 $nm^2$, at least 1 molecule per 3,000 $nm^2$, at least 1 molecule per 2,000 $nm^2$, at least 1 molecule per 1,000 $nm^2$, or at least 1 molecule per 500 $nm^2$.

The graphene substrate typically has an area of at least 500 $nm^2$. In certain cases, the area of the graphene substrate is at least 1 $\mu m^2$, at least 10 $\mu m^2$, at least 100 $\mu m^2$, at least 1,000 $\mu m^2$, at least 2,000 $\mu m^2$, at least 3,000 $\mu m^2$, at least 4,000 $\mu m^2$, at least 5,000 $\mu m^2$, or at least 10,000 $\mu m^2$.

Figure 21:
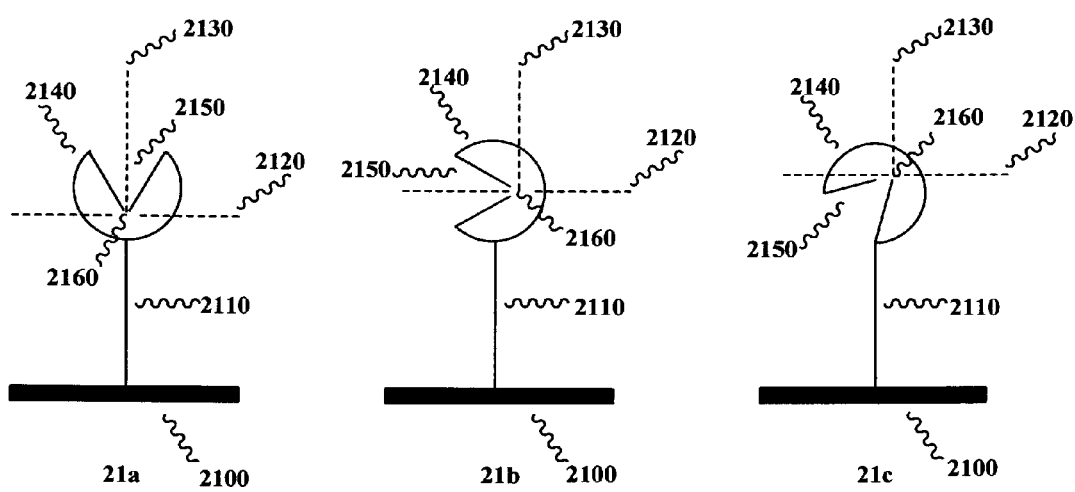
FIG. 21 is an illustration of a molecule (2140) bound to a graphene substrate (2100) through a bond (2110) where a binding site (2150) on the molecule is defined by the intersection of dashed lines 2120 and 2130, which run through the center of the binding site (2160) in perpendicular directions.

FIG. 21 is an illustration of a molecule (2140) bound to a graphene substrate (2100) through a bond (2110), where a binding site (2150) on the molecule is defined by the intersection of dashed lines 2120 and 2130, which run through the center of the binding site (2160) in perpendicular directions. The functionalized graphene substrate (2100) of the present invention may include many different molecules having binding sites on its non-edge regions. With respect to molecules (2140), in the present invention more than twenty percent of them are bound in such a way that a conformation where the center of their binding site (2160) is bisected by line 2120 (as shown in FIG. 21b) is accessible at an energy level that is less than 20 kcal/mol above the conformational ground state. In certain cases, more than thirty percent, forty percent, or fifty percent are bound in that way. In certain cases the accessible energy level is less than 15 kcal/mol above the conformational ground state or 10 kcal/mol above the conformational ground state.

Figure 22:
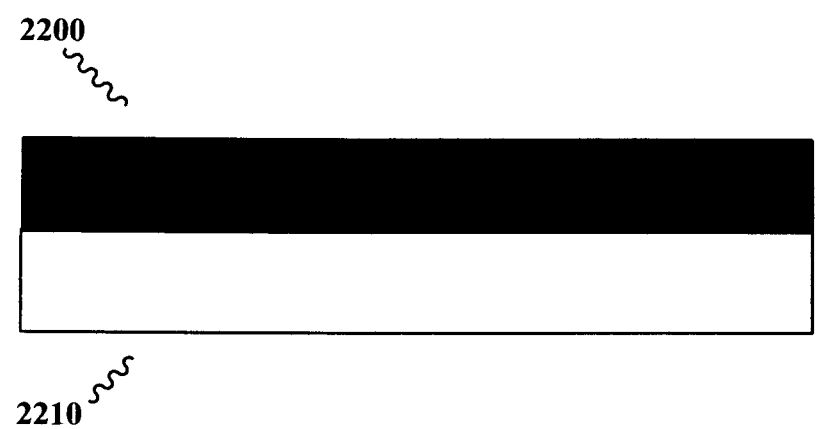
FIG. 22 is an illustration of a side view of a graphene substrate (2200) adhered to a supporting substrate (2210).

In certain cases, the graphene substrate of the present invention is adhered to a supporting substrate. FIG. 22 is an illustration of a side view of a graphene substrate (2200) adhered to a supporting substrate (2210). One method of forming a graphene substrate on a metallic or dielectric supporting substrate is discussed in US Pat. Appl. Pub. No. 20110091647, which was published on Apr. 21, 2011, and which is incorporated-by-reference for all purposes into this document. The graphene substrate synthesis method involves heating a metal or a dielectric on a substrate to a temperature between 400° C. and 1,400° C. The metal or dielectric is then exposed to an organic compound using chemical vapor deposition, thereby growing graphene on the metal or dielectric.

One method by which edge regions can be created internally, within a graphene substrate involves the creation of apertures or holes. The creation of such apertures or holes is discussed in US Pat. Appl. Pub. No. 20120048894, which was published on Mar. 1, 2012, and which is incorporated-by-reference for all purposes into this document. According to the publication, holes or apertures can be made by selective oxidation or be laser-drilled. Using the oxidation method discussed in *Nano Lett.* 2008, Vol. 8, No. 7, pgs 1965-1970, applicants were able to form apertures or holes in the 20 to 180 nm range in graphene substrates.

Furthermore, one may use, for example, a nanomeshed graphene substrate, which provides internal edge regions. The formation of such nanomeshes is discussed in US Pat. Appl. Pub. No. 20120301953, which was published on Nov. 29, 2012, and which is incorporated-by-reference for all purposes into this document.

The invention claimed is:

1. A graphene substrate, wherein the substrate comprises edge and non-edge regions, and wherein organic or inorganic molecules are bound to a nucleophilic moiety covalently linked to a carbon molecule in the non-edge regions of the substrate, and wherein the organic or inorganic molecules are present on the non-edge regions at a population greater than about one molecule per 30,000 $nm^2$.

2. The graphene substrate according to claim 1, wherein organic molecules are present on the substrate, and wherein the organic molecules are selected from a group consisting of: antibodies; antibody fragments; aptamers; large molecule therapeutics; oligonucleotides; oligopeptides; oligosaccharides, proteins and small molecule therapeutics.

3. The graphene substrate according to claim 2, wherein the population is greater than about 1 molecule per 10,000 $nm^2$.

4. The graphene substrate according to claim 3, wherein the organic molecules are selected from a group consisting of: antibodies; antibody fragments; proteins; and, aptamers.

5. The graphene substrate according to claim 3, wherein the organic molecules are selected from a group consisting of: large molecule therapeutics; oligonucleotides; oligopeptides; oligosaccharides and small molecule therapeutics.

6. The graphene substrate according to claim 4, wherein the population is greater than about 1 molecule per 3,000 $nm^2$.

7. The graphene substrate according to claim 5, wherein the population is greater than about 1 molecule per 3,000 $nm^2$.

8. The graphene substrate according to claim 6, wherein the organic molecules are proteins, and wherein the proteins are selected from a group consisting of: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1b; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab; DNA polymerase.

9. The graphene substrate according to claim 7, wherein the organic molecules are large molecule therapeutics, and wherein the large molecule therapeutics are selected from a group consisting of: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-glucosidase inhibitors; amebicides; aminoglycosides; aminopenicillins; aminosalicylates; AMPA receptor antagonists; amylin analogs; analgesics; androgens and anabolic steroids; angiotensin converting enzyme inhibitors; angiotensin II inhibitors; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiarrheals; antidiuretic hormones; antiemetic/antivertigo agents; antifungals; antigonadotropic agents; antigout agents; antihistamines; antihyperlipidemic agents; antihyperuricemic agents; antimalarial agents; antimalarial combinations; antimalarial quinolines; antimetabolites; antimigraine agents; antineoplastic detoxifying agents; antineoplastic interferons; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; bisphosphonates; bone resorption inhibitors; bronchodilators; calcineurin inhibitors; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD30 monoclonal antibodies; CD33 monoclonal antibodies; CD52 monoclonal antibodies; central nervous system agents; cephalosporins; cerumenolytics; CFTR potentiators; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; dibenzazepine anticonvulsants; digestive enzymes; dipeptidyl peptidase 4 inhibitors; diuretics; dopaminergic antiparkinsonism agents; echinocandins; EGFR inhibitors; estrogen receptor antagonists; estrogens; factor Xa inhibitors; fatty acid derivative anticonvulsants; fibric acid derivatives; first generation cephalosporins; fourth generation cephalosporins; gamma-aminobutyric acid analogs; gamma-aminobutyric acid reuptake inhibitors; gastrointestinal agents; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; guanylate cyclase-C agonists; *H. pylori* eradication agents; H2 antagonists; hedgehog pathway inhibitorshematopoietic stem cell mobilizer; heparin antagonists; heparins; HER2 inhibitors; histone deacetylase inhibitors; hormones; hormones/antineoplastics; hydantoin anticonvulsants; hydrazide derivatives; immune globulins; immunologic agents; immunostimulants; immunosuppressive agents; incretin mimetics; inotropic agents; insulin; insulin-like growth factor; integrase strand transfer inhibitor; interferons; interleukin inhibitors; interleukins; ketolides; leprostatics; leukotriene modifiers; lincomycin derivatives; loop diuretics; lymphatic staining agents; lysosomal enzymes; macrolide derivatives; macrolides; mast cell stabilizers; meglitinides; metabolic agents; methylxanthines; mineralocorticoids; mitotic inhibitors; monoamine oxidase inhibitors; mTOR inhibitors; mucolytics; multikinase inhibitors; muscle relaxants; mydriatics; narcotic analgesics; natural penicillins; neuraminidase inhibitors; neuromuscular blocking agents; neuronal potassium channel openers; next generation cephalosporins; nicotinic acid derivatives; NNRTIs; non-cardioselective beta blockers; non-sulfonylureas; nonsteroidal anti-inflammatory agents; nucleoside reverse transcriptase inhibitors (NRTIs); oxazolidinedione anticonvulsants; parathyroid hormone and analogs; penicillinase resistant penicillins; penicillins; peripheral opioid receptor antagonists; peripheral vasodilators; peripherally acting anti-obesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proteasome inhibitors; proton pump inhibitors; psoralens; psychotherapeutic agents; purine nucleosides; pyrrolidine anticonvulsants; quinolones; recombinant human erythropoietins; renin inhibitors; respiratory agents; rifamycin derivatives; salicylates; sclerosing agents; second generation cephalosporins; selective estrogen receptor modulators; selective immunosuppressants; selective phosphodiesterase-4 inhibitors; selective serotonin reuptake inhibitors; serotonin-norepinephrine reuptake inhibitors; serotoninergic neuroenteric modulators; sex hormone combinations; sex hormones; SGLT-2 inhibitors; skeletal muscle relaxants; smoking cessation agents; somatostatin and somatostatin analogs; statins; *streptomyces* derivatives; succinimide anticonvulsants; sulfonamides; sulfonylureas; synthetic ovulation stimulants; tetracyclic antidepressants; tetracyclines; therapeutic radiopharmaceuticals; therapeutic vaccines; thiazide diuretics;

thiazolidinediones; thioxanthenes; third generation cephalosporins; thrombin inhibitors; thrombolytics; thyroid drugs; TNF alfa inhibitors; tocolytic agents; triazine anticonvulsants; tricyclic antidepressants; trifunctional monoclonal antibodies; urea anticonvulsants; urea cycle disorder agents; urinary anti-infectives; urinary antispasmodics; vasodilators; vasopressin antagonists; vasopressors; VEGF/VEGFR inhibitors; viral vaccines.

10. The graphene substrate according to claim 7, wherein the organic molecules are oligonucleotides, and wherein the oligonucleotides are selected from a group consisting of:

$N_1N_2N_3N_4N_5N_6N_7N_8N_9N_{10}N_{11}N_{12}N_{13}N_{14}N_{15}N_{16}N_{17}N_{18}N_{19}N_{20}$ where $N_1$ is A, T, C or G; $N_2$ is A, T, C or G; $N_3$ is A, T, C or G; $N_4$ is A, T, C or G; $N_5$ is A, T, C, G, or no base; $N_6$ is A, T, C, G, or no base; $N_7$ is A, T, C, G, or no base; $N_8$ is A, T, C, G, or no base; $N_9$ is A, T, C, G, or no base; $N_{10}$ is A, T, C, G, or no base; $N_{11}$ is A, T, C, G, or no base; $N_{12}$ is A, T, C, G, or no base; $N_{13}$ is A, T, C, G, or no base; $N_{14}$ is A, T, C, G, or no base; $N_{15}$ is A, T, C, G, or no base; $N_{16}$ is A, T, C, G, or no base; $N_{17}$ is A, T, C, G, or no base; $N_{18}$ is A, T, C, G, or no base; $N_{19}$ is A, T, C, G, or no base; $N_{20}$ is A, T, C, G, or no base.

11. The graphene substrate according to claim 7, wherein the organic molecules are oligopeptides, and wherein the oligopeptides are selected from a group consisting of:

$P_1P_2P_3P_4P_5P_6P_7P_8P_9P_{10}P_{11}P_{12}P_{13}P_{14}P_{15}P_{16}P_{17}P_{18}P_{19}P_{20}P_{21}P_{22}P_{23}P_{24}P_{25}$ where $P_1$ is G, P, A, V, L, I M, C, R, Y, W, H, K, R, Q, N, E, D, S or T; $P_2$ is G, P, A, V, L, I M, C, R, Y, W, H, K, R, Q, N, E, D, S or T; $P_3$ is G, P, A, V, L, I M, C, R, Y, W, H, K, R, Q, N, E, D, S or T; $P_4$ is G, P, A, V, L, I M, C, R, Y, W, H, K, R, Q, N, E, D, S or T; $P_5$ is G, P, A, V, L, I M, C, R, Y, W, H, K, R, Q, N, E, D, S or T; $P_6$ is G, P, A, V, L, I M, C, R, Y, W, H, K, R, Q, N, E, D, S, T or no amino acid; $P_7$ is G, P, A, V, L, I M, C, R, Y, W, H, K, R, Q, N, E, D, S, T or no amino acid; $P_8$ is G, P, A, V, L, I M, C, R, Y, W, H, K, R, Q, N, E, D, S, T or no amino acid; $P_9$ is G, P, A, V, L, I M, C, R, Y, W, H, K, R, Q, N, E, D, S, T or no amino acid; $P_{10}$ is G, P, A, V, L, I M, C, R, Y, W, H, K, R, Q, N, E, D, S, T or no amino acid; $P_{11}$ is G, P, A, V, L, I M, C, R, Y, W, H, K, R, Q, N, E, D, S, T or no amino acid; $P_{12}$ is G, P, A, V, L, I M, C, R, Y, W, H, K, R, Q, N, E, D, S, T or no amino acid; $P_{13}$ is G, P, A, V, L, I M, C, R, Y, W, H, K, R, Q, N, E, D, S, T or no amino acid; $P_{14}$ is G, P, A, V, L, I M, C, R, Y, W, H, K, R, Q, N, E, D, S, T or no amino acid; $P_{15}$ is G, P, A, V, L, I M, C, R, Y, W, H, K, R, Q, N, E, D, S, T or no amino acid; $P_{16}$ is G, P, A, V, L, I M, C, R, Y, W, H, K, R, Q, N, E, D, S, T or no amino acid; $P_{17}$ is G, P, A, V, L, I M, C, R, Y, W, H, K, R, Q, N, E, D, S, T or no amino acid; $P_{18}$ is G, P, A, V, L, I M, C, R, Y, W, H, K, R, Q, N, E, D, S, T or no amino acid; $P_{19}$ is G, P, A, V, L, I M, C, R, Y, W, H, K, R, Q, N, E, D, S, T or no amino acid; $P_{20}$ is G, P, A, V, L, I M, C, R, Y, W, H, K, R, Q, N, E, D, S, T or no amino acid; $P_{21}$ is G, P, A, V, L, I M, C, R, Y, W, H, K, R, Q, N, E, D, S, T or no amino acid; $P_{22}$ is G, P, A, V, L, I M, C, R, Y, W, H, K, R, Q, N, E, D, S, T or no amino acid; $P_{23}$ is G, P, A, V, L, I M, C, R, Y, W, H, K, R, Q, N, E, D, S, T or no amino acid; $P_{24}$ is G, P, A, V, L, I M, C, R, Y, W, H, K, R, Q, N, E, D, S, T or no amino acid; $P_{25}$ is G, P, A, V, L, I M, C, R, Y, W, H, K, R, Q, N, E, D, S, T or no amino acid.

12. The graphene substrate according to claim 7, wherein the organic molecules are oligosaccharides, and wherein the oligosaccharides are selected from a group consisting of:

$S_1S_2S_3S_4S_5S_6S_7S_8S_9S_{10}S_{11}S_{12}S_{13}S_{14}S_{15}S_{16}S_{17}S_{18}S_{19}S_{20}S_{21}S_{22}S_{23}S_{24}S_{25}$ where $S_1$ is glucose, fructose, glucopyranose, ribitol, gluconic acid, glucosamine, or N-acetylneuraminide; $S_2$ is glucose, fructose, glucopyranose, ribitol, gluconic acid, glucosamine, or N-acetylneuraminide; $S_3$ is glucose, fructose, glucopyranose, ribitol, gluconic acid, glucosamine, N-acetylneuraminide or no monosaccharide; $S_4$ is glucose, fructose, glucopyranose, ribitol, gluconic acid, glucosamine, N-acetylneuraminide or no monosaccharide; $S_5$ is glucose, fructose, glucopyranose, ribitol, gluconic acid, glucosamine, N-acetylneuraminide or no monosaccharide; $S_6$ is glucose, fructose, glucopyranose, ribitol, gluconic acid, glucosamine, N-acetylneuraminide or no monosaccharide; $S_7$ is glucose, fructose, glucopyranose, ribitol, gluconic acid, glucosamine, N-acetylneuraminide or no monosaccharide; $S_8$ is glucose, fructose, glucopyranose, ribitol, gluconic acid, glucosamine, N-acetylneuraminide or no monosaccharide; $S_9$ is glucose, fructose, glucopyranose, ribitol, gluconic acid, glucosamine, N-acetylneuraminide or no monosaccharide; $S_{10}$ is glucose, fructose, glucopyranose, ribitol, gluconic acid, glucosamine, N-acetylneuraminide or no monosaccharide; $S_{11}$ is glucose, fructose, glucopyranose, ribitol, gluconic acid, glucosamine, N-acetylneuraminide or no monosaccharide; $S_{12}$ is glucose, fructose, glucopyranose, ribitol, gluconic acid, glucosamine, N-acetylneuraminide or no monosaccharide; $S_{13}$ is glucose, fructose, glucopyranose, ribitol, gluconic acid, glucosamine, N-acetylneuraminide or no monosaccharide; $S_{14}$ is glucose, fructose, glucopyranose, ribitol, gluconic acid, glucosamine, N-acetylneuraminide or no monosaccharide; $S_{15}$ is glucose, fructose, glucopyranose, ribitol, gluconic acid, glucosamine, N-acetylneuraminide or no monosaccharide; $S_{16}$ is glucose, fructose, glucopyranose, ribitol, gluconic acid, glucosamine, N-acetylneuraminide or no monosaccharide; $S_{17}$ is glucose, fructose, glucopyranose, ribitol, gluconic acid, glucosamine, N-acetylneuraminide or no monosaccharide; $S_{18}$ is glucose, fructose, glucopyranose, ribitol, gluconic acid, glucosamine, N-acetylneuraminide or no monosaccharide; $S_{19}$ is glucose, fructose, glucopyranose, ribitol, gluconic acid, glucosamine, N-acetylneuraminide or no monosaccharide; $S_{20}$ is glucose, fructose, glucopyranose, ribitol, gluconic acid, glucosamine, N-acetylneuraminide or no monosaccharide; $S_{21}$ is glucose, fructose, glucopyranose, ribitol, gluconic acid, glucosamine, N-acetylneuraminide or no monosaccharide; $S_{22}$ is glucose, fructose, glucopyranose, ribitol, gluconic acid, glucosamine, N-acetylneuraminide or no monosaccharide; $S_{23}$ is glucose, fructose, glucopyranose, ribitol, gluconic acid, glucosamine, N-acetylneuraminide or no monosaccharide; $S_{24}$ is glucose, fructose, glucopyranose, ribitol, gluconic acid, glucosamine, N-acetylneuraminide or no monosaccharide; $S_{25}$ is glucose, fructose, glucopyranose, ribitol, gluconic acid, glucosamine, N-acetylneuraminide or no monosaccharide.

13. The graphene substrate according to claim 7, wherein the organic molecules are small molecule therapeutics, and wherein the small molecule therapeutics are selected from a group consisting of: 5-alpha-reductase inhibitors; 5-aminosalicylates; 5HT3 receptor antagonists; adamantane antivirals; adrenal cortical steroids; adrenal corticosteroid inhibitors; adrenergic bronchodilators; agents for hypertensive emergencies; agents for pulmonary hypertension; aldosterone receptor antagonists; alkylating agents; alpha-glucosidase inhibitors; alternative medicines; amebicides; aminoglycosides; aminopenicillins; aminosalicylates; AMPA receptor antagonists; amylin analogs; analgesics; androgens and anabolic steroids; angiotensin converting enzyme inhibitors; angiotensin II inhibitors; anorexiants; antacids; anthelmintics; anti-angiogenic ophthalmic agents; anti-CTLA-4 monoclonal antibodies; anti-infectives; antiadrenergic agents, centrally acting; antiadrenergic agents, peripherally acting; antiandrogens; antianginal agents; antiarrhythmic agents; antiasthmatic combinations; antibiotics/antineoplastics; anticholinergic antiemetics; anticholinergic antiparkinson agents; anticholinergic bronchodilators; anticholinergic chronotropic agents; anticholinergics/antispasmodics; anticoagulants; anticonvulsants; antidepressants; antidiabetic agents; antidiarrheals; antidiuretic hormones; antiemetic/antivertigo agents; antifungals; antigonadotropic agents; antigout agents; antihistamines; antihyperlipidemic agents; antihyperuricemic agents; antimalarial agents; antimalarial combinations; antimalarial quinolines; antimetabolites; antimigraine agents; antineoplastic detoxifying agents; antineoplastic interferons; antineoplastics; antiparkinson agents; antiplatelet agents; antipseudomonal penicillins; antipsoriatics; antipsychotics; antirheumatics; antiseptic and germicides; antithyroid agents; antitoxins and antivenins; antituberculosis agents; antituberculosis combinations; antitussives; antiviral agents; antiviral interferons; anxiolytics, sedatives, and hypnotics; aromatase inhibitors; atypical antipsychotics; azole antifungals; bacterial vaccines; barbiturate anticonvulsants; barbiturates; BCR-ABL tyrosine kinase inhibitors; benzodiazepine anticonvulsants; benzodiazepines; beta-adrenergic blocking agents; beta-lactamase inhibitors; bile acid sequestrants; bisphosphonates; bone resorption inhibitors; bronchodilators; calcineurin inhibitors; calcitonin; calcium channel blocking agents; carbamate anticonvulsants; carbapenems; carbonic anhydrase inhibitor anticonvulsants; carbonic anhydrase inhibitors; cardiac stressing agents; cardioselective beta blockers; cardiovascular agents; catecholamines; CD20 monoclonal antibodies; CD30 monoclonal antibodies; CD33 monoclonal antibodies; CD52 monoclonal antibodies; central nervous system agents; cephalosporins; cerumenolytics; CFTR potentiators; chemokine receptor antagonist; chloride channel activators; cholesterol absorption inhibitors; cholinergic agonists; cholinergic muscle stimulants; cholinesterase inhibitors; CNS stimulants; coagulation modifiers; colony stimulating factors; contraceptives; corticotropin; coumarins and indandiones; cox-2 inhibitors; dibenzazepine anticonvulsants; digestive enzymes; dipeptidyl peptidase 4 inhibitors; diuretics; dopaminergic antiparkinsonism agents; echinocandins; EGFR inhibitors; estrogen receptor antagonists; estrogens; factor Xa inhibitors; fatty acid derivative anticonvulsants; fibric acid derivatives; first generation cephalosporins; fourth generation cephalosporins; gamma-aminobutyric acid analogs; gamma-aminobutyric acid reuptake inhibitors; gastrointestinal agents; genitourinary tract agents; GI stimulants; glucocorticoids; glucose elevating agents; glycopeptide antibiotics; glycoprotein platelet inhibitors; glycylcyclines; gonadotropin releasing hormones; gonadotropin-releasing hormone antagonists; gonadotropins; group I antiarrhythmics; group II antiarrhythmics; group III antiarrhythmics; group IV antiarrhythmics; group V antiarrhythmics; growth hormone receptor blockers; growth hormones; guanylate cyclase-C agonists; *H. pylori* eradication agents; H2 antagonists; hedgehog pathway inhibitorshematopoietic stem cell mobilizer; heparin antagonists; heparins; HER2 inhibitors; histone deacetylase inhibitors; hormones; hormones/antineoplastics; hydantoin anticonvulsants; hydrazide derivatives; immune globulins; immunologic agents; immunostimulants; immunosuppressive agents; incretin mimetics; inotropic agents; insulin; insulin-like growth factor; integrase strand transfer inhibitor; interferons; interleukin inhibitors; interleukins; ketolides; leprostatics; leukotriene modifiers; lincomycin derivatives; loop diuretics; lymphatic staining agents; lysosomal enzymes; macrolide derivatives; macrolides; mast cell stabilizers; meglitinides; metabolic agents; methylxanthines; mineralocorticoids; mitotic inhibitors; monoamine oxidase inhibitors; mTOR inhibitors; mucolytics; multikinase inhibitors; muscle relaxants; mydriatics; narcotic analgesics; natural penicillins; neuraminidase inhibitors; neuromuscular blocking agents; neuronal potassium channel openers; next generation cephalosporins; nicotinic acid derivatives; NNRTIs; non-cardioselective beta blockers; non-sulfonylureas; nonsteroidal anti-inflammatory agents; nucleoside reverse transcriptase inhibitors (NRTIs); oxazolidinedione anticonvulsants; parathyroid hormone and analogs; penicillinase resistant penicillins; penicillins; peripheral opioid receptor antagonists; peripheral vasodilators; peripherally acting antiobesity agents; phenothiazine antiemetics; phenothiazine antipsychotics; phenylpiperazine antidepressants; plasma expanders; platelet aggregation inhibitors; platelet-stimulating agents; polyenes; potassium-sparing diuretics; probiotics; progesterone receptor modulators; progestins; prolactin inhibitors; prostaglandin D2 antagonists; protease inhibitors; proteasome inhibitors; proton pump inhibitors; psoralens; psychotherapeutic agents; purine nucleosides; pyrrolidine anticonvulsants; quinolones; recombinant human erythropoietins; renin inhibitors; respiratory agents; rifamycin derivatives; salicylates; sclerosing agents; second generation cephalosporins; selective estrogen receptor modulators; selective immunosuppressants; selective phosphodiesterase-4 inhibitors; selective serotonin reuptake inhibitors; serotonin-norepinephrine reuptake inhibitors; serotoninergic neuroenteric modulators; sex hormone combinations; sex hormones; SGLT-2 inhibitors; skeletal muscle relaxants; smoking cessation agents; somatostatin and somatostatin analogs; statins; *streptomyces* derivatives; succinimide anticonvulsants; sulfonamides; sulfonylureas; synthetic ovulation stimulants; tetracycline antidepressants; tetracyclines; therapeutic radiopharmaceuticals; therapeutic vaccines; thiazide diuretics; thiazolidinediones; thioxanthenes; third generation cephalosporins; thrombin inhibitors; thrombolytics; thyroid drugs; TNF alfa inhibitors; tocolytic agents; triazine anticonvulsants; tricyclic antidepressants; trifunctional monoclonal antibodies; urea anticonvulsants; urea cycle disorder agents; urinary anti-infectives; urinary antispasmodics; vasodilators; vasopressin antagonists; vasopressors; VEGF/VEGFR inhibitors; viral vaccines.

14. A method of functionalizing a graphene substrate, wherein the method comprises the steps of:
   a) obtaining a graphene substrate that has edge regions and non-edge regions, wherein the non-edge regions comprise epoxy moieties;
   b) reacting the epoxy moieties with a Nu-M, wherein Nu is a nucleophilic moiety and M is an attached organic or inorganic moiety,
   thereby functionalizing the graphene substrate.

15. The method according to claim 14, wherein Nu is $NH_2$, and wherein M is an attached organic moiety, and wherein the organic moiety is selected from a group of organic moieties consisting of: an antibody; a linking group attached to an antibody; an antibody fragment; a linking group attached to an antibody fragment; a linking group attached to an aptamer; a protein; a linking group attached to a protein; an oligopeptide; a linking group attached to an oligopeptide; a linking group attached to an oligosaccharide; a large molecule therapeutic; a linking group attached to a large molecule therapeutic; a small molecule therapeutic; a linking group attached to a small molecule therapeutic.

16. The method according to claim 15, wherein the organic molecule is a linking group attached to a protein, and wherein the protein is selected from a group consisting of: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1b; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab; DNA polymerase.

17. The method according to claim 16, wherein the functionalized graphene substrate has a population of organic molecules at the non-edge regions of at least 1 per 30,000 nm².

18. The method according to claim 17, wherein the functionalized graphene substrate has a population of organic molecules at the non-edge regions of at least 1 per 10,000 nm².

19. A method of functionalizing a graphene substrate, wherein the method comprises the steps of:
   a) obtaining a graphene substrate that has edge regions and non-edge regions, wherein the non-edge regions comprise hydroxy moieties;
   b) reacting the hydroxyl moieties with a E-M, wherein E is an electrophilic moiety and M is an attached organic or inorganic moiety,
   thereby functionalizing the graphene substrate.

20. The method according to claim 19, wherein EM is OCN-Protein, wherein the N atom is part of the protein, and wherein the protein is selected from a group of proteins consisting of: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1b; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab; DNA polymerase.

21. The method according to claim 20, wherein the functionalized graphene substrate has a population of organic molecules at the non-edge regions of at least 1 per 30,000 nm².

22. The method according to claim 21, wherein the functionalized graphene substrate has a population of organic molecules at the non-edge regions of at least 1 per 10,000 nm².

23. A method of functionalizing a graphene substrate, wherein the method comprises the steps of:
   1. obtaining a graphene substrate that has edge regions and non-edge regions;
   2. reacting the substrate with a molecule that comprises a histidine, arginine, lysine or cationic tag covalently attached to it
   thereby providing a functionalized graphene substrate, wherein molecules are non-covalently attached to the non-edge regions of the substrate.

24. The method according to claim 23, wherein the molecule is a protein, and wherein the protein is selected from a group of proteins consisting of: Insulin; Pramlintide; Growth hormone; Mecasermin; Factor VIII; Factor IX; Antithrombin III; Protein C; B-Gluco-cerebrosidase; Alglucosidase-α; Laronidase; Idursulphase; Galsulphase; Agalsidase-β; A-1-Proteinase inhibitor; Lactase; Lipase; Amylase; Protease; Adenosine deaminase; Human albumin; Erythropoietin; Darbepoetin-α; Filgrastim; Sargramostim; Oprelvekin; Human follicle-stimulating hormone; Human chorionic gonadotropin; Lutropin-α; Type I α-interferon; Interferon-α2a; Interferon-α2b; Interferon-αn3; Interferon-β1a; Interferon-β1b; Interferon-γ1b; Aldesleukin; Alteplase; Reteplase; Tenecteplase; Urokinase; Factor VIIa; Drotrecogin-α; Salmon calcitonin; Teriparatide; Exenatide; Octreotide; Dibotermin-α; Recombinant human bone morphogenic protein 7; Histrelin; Palifermin; Becaplermin; Trypsin; Nesiritide; Botulinum toxin type A; Botulinum toxin type B; Collagenase; Human deoxy-ribonuclease I; Hyaluronidase; Papain; L-Asparaginase; Rasburicase; Lepirudin; Bivalirudin; Streptokinase; Anistreplase; Bevacizumab; Cetuximab; Panitumumab; Alemtuzumab; Rituximab; Trastuzumab; Abtacept; Anakinra; Adalimumab; Etanercept; Infliximab; Alefacept; Efalizumab; Natalizumab; Eculizumab; Antithymocyte globulin; Basiliximab; Daclizumab; Muromonab-CD3; Omalizumab; Palivizumab; Enfuvirtide; Abciximab; Pegvisomant; Crotalidae polyvalent immune Fab; Digoxin immune serum Fab; Ranibizumab; Denileukin diftitox; Ibritumomab tiuxetan; Gemtuzumab ozogamicin; Tositumomab; DNA polymerase.

25. The method according to claim 24, wherein the functionalized graphene substrate has a population of organic molecules at the non-edge regions of at least 1 per 30,000 nm.

* * * * *